United States Patent
Baraznenok et al.

(10) Patent No.: US 12,365,891 B2
(45) Date of Patent: Jul. 22, 2025

(54) METHODS AND COMPOSITIONS FOR NUCLEIC ACID ISOLATION

(71) Applicant: Cepheid, Sunnyvale, CA (US)

(72) Inventors: Vera Baraznenok, Sunnyvale, CA (US); Alex I. Kutyavin, Sunnyvale, CA (US); Oliver Z. Nanassy, Sunnyvale, CA (US); Dmitri Sergueev, Sunnyvale, CA (US); Alexander A. Gall, Sunnyvale, CA (US)

(73) Assignee: CEPHEID, Sunnyvale, CA (US)

( * ) Notice: Subject to any disclaimer, the term of this patent is extended or adjusted under 35 U.S.C. 154(b) by 1051 days.

(21) Appl. No.: 17/269,182

(22) PCT Filed: Aug. 16, 2019

(86) PCT No.: PCT/US2019/046908
§ 371 (c)(1),
(2) Date: Feb. 17, 2021

(87) PCT Pub. No.: WO2020/037260
PCT Pub. Date: Feb. 20, 2020

(65) Prior Publication Data
US 2021/0324372 A1 Oct. 21, 2021

Related U.S. Application Data

(60) Provisional application No. 62/765,013, filed on Aug. 17, 2018.

(51) Int. Cl.
C12N 15/10 (2006.01)
C12Q 1/6806 (2018.01)
C08B 37/00 (2006.01)

(52) U.S. Cl.
CPC ....... C12N 15/1006 (2013.01); C12Q 1/6806 (2013.01); C08B 37/0045 (2013.01)

(58) Field of Classification Search
CPC ............ C12N 15/1006; C12N 15/1013; C12N 15/1017; C08B 37/0045; C08B 37/0063; C08B 37/0066; C08B 37/0069; C08B 37/0072; C08B 37/0075
See application file for complete search history.

(56) References Cited

U.S. PATENT DOCUMENTS

| | | | |
|---|---|---|---|
| 5,384,400 A | 1/1995 | Crescenzi | |
| 5,763,186 A | 6/1998 | Ludtke | |
| 6,374,684 B1 | 4/2002 | Dority | |
| 7,125,842 B2 | 10/2006 | Kawabe | |
| 9,663,779 B2 | 5/2017 | Fabis et al. | |
| 11,819,584 B2 | 11/2023 | Kutyavin et al. | |
| 2004/0191790 A1 | 9/2004 | Tomassen | |
| 2005/0119450 A1* | 6/2005 | Wang | A61P 11/06 528/398 |
| 2005/0130196 A1 | 6/2005 | Hofstadler | |
| 2005/0163825 A1 | 7/2005 | Naidu | |
| 2006/0127991 A1 | 6/2006 | Christensen | |
| 2008/0317666 A1* | 12/2008 | Fattal | A61P 35/00 424/9.1 |
| 2011/0054161 A1 | 3/2011 | Bitner | |
| 2011/0117628 A1 | 5/2011 | Hillebrand | |
| 2012/0245337 A1 | 9/2012 | Fabis et al. | |
| 2013/0072381 A1 | 3/2013 | Trudsoe | |
| 2014/0011201 A1 | 1/2014 | Richmond | |
| 2014/0243216 A1 | 8/2014 | Fabis et al. | |
| 2015/0093755 A1 | 4/2015 | Zhao | |
| 2015/0275269 A1 | 10/2015 | Li et al. | |
| 2017/0320764 A1 | 11/2017 | De Boer | |
| 2017/0335312 A1 | 11/2017 | Hillebrand | |
| 2021/0238583 A1 | 8/2021 | Kutyavin et al. | |

FOREIGN PATENT DOCUMENTS

| | | |
|---|---|---|
| AU | 2015201538 | 4/2015 |
| CN | 1680421 | 10/2005 |
| CN | 1798570 | 7/2006 |
| CN | 101018870 | 8/2007 |
| CN | 101232807 | 7/2008 |
| CN | 101573144 | 11/2009 |
| CN | 103333870 | 10/2013 |
| CN | 107141369 | 9/2017 |
| CN | 107690481 | 2/2018 |
| CN | 108219026 | 6/2018 |
| CN | 111868253 | 10/2020 |
| CN | 113015800 A | 6/2021 |
| CN | 113056291 | 6/2021 |
| CN | 113056291 A | 6/2021 |
| DE | 69321215 | 6/1999 |
| EP | 1613733 | 1/2006 |
| JP | 2012513385 A | 6/2012 |
| JP | 2013502934 | 1/2013 |
| JP | 2013502934 A | 1/2013 |
| JP | 2018518150 | 7/2018 |

(Continued)

OTHER PUBLICATIONS

Rubinstein et al., "In Vitro Evaluation of Calcium Pectinate: A Potential Colon-Specific Drug Delivery Carrier" Pharmaceutical Research vol. 10 No. 2 pp. 258-263 (Year: 1993).*
Khaled et al., "One-pot synthesis of pH-responsive hybrid nanogel particles for the intracellular delivery of small interfering RNA" Biomaterials vol. 87 pp. 57-68, DOI: 10.1016/j.biomaterials.2016.01.052 (Year: 2016).*
Prestwich, "Hyaluronic acid-based clinical biomaterials derived for cell and molecule delivery in regenerative medicine" Journal of Controlled Release vol. 155 pp. 193-199, DOI: 10.1016/j.jconrel.2011.04.007 (Year: 2011).*
First Examination Report mailed Jul. 5, 2023, in corresponding Indian Application No. 202137010967, filed Aug. 16, 2019, 11 pages.

(Continued)

*Primary Examiner* — Eric Olson
(74) *Attorney, Agent, or Firm* — McAndrews, Held & Malloy, Ltd.

(57) ABSTRACT

Methods and compositions for isolation of nucleic acids from biological samples are provided.

19 Claims, No Drawings

Specification includes a Sequence Listing.

(56) References Cited

FOREIGN PATENT DOCUMENTS

| WO | 2001038516 | | 5/2001 | | |
| WO | 2004005352 | | 1/2004 | | |
| WO | WO-2010138074 | A1 * | 12/2010 | ........... | A61K 31/726 |
| WO | 2011/151428 | A1 | 8/2011 | | |
| WO | WO-2015082495 | A1 * | 6/2015 | ............ | B01D 15/12 |
| WO | 2015120445 | | 8/2015 | | |

OTHER PUBLICATIONS

Notice of Reasons for Refusal mailed Aug. 8, 2023, in corresponding Japanese Application No. 2021-507772, filed Aug. 16, 2019, 7 pages.

Office Action mailed Dec. 6, 2023, in corresponding Canadian Application No. 3,109,805, filed Aug. 16, 2019, 4 pages.

Notice of Reasons for Refusal mailed Jan. 19, 2024, in corresponding Japanese Application No. 2021-507772, filed Aug. 16, 2019, 8 pages.

European Patent Office, International Search Report issued in PCT/US2019/046908, Nov. 15, 2019, 5 pages.

European Patent Office, Written Opinion issued in PCT/US2019/046908, Nov. 15, 2019, 5 pages.

The International Bureau of WIPO, International Preliminary Report on Patentability issued in PCT/US2019/046908, Feb. 23, 2021, 6 pages.

Kunal R. Pandit, et al., "Capture and Direct Amplification of DNA on Chitosan Microparticles in a Single PCR-Optimal Solution," Analytical Chemistry, vol. 87, No. 21, Oct. 13, 2015, pp. 11022-11029.

First Office Action mailed Jun. 26, 2024, issued in the corresponding Chinese Application No. 201980065415.8; 9 pages.

Second Office Action, Chinese Application No. 2019800654158, dated Jan. 9, 2025, 10 pages.

Marcello Lenucci et al., Do Polyamines, Contribute to Plant Cell Wall Assembly by Forming Amide Bonds With Pectins?, Phytochemistry, vol. 66, 2005, pp. 2581-2594.

U.S. Appl. No. 17/269,198—European Patent Office, International Search Report issued in International Application No. PCT/US2019/046912, Oct. 29, 2019, 4 pages.

U.S. Appl. No. 17/269,198—European Patent Office, Written Opinion of the International Searching Authority issued in International Application No. PCT/US2019/046912, Oct. 29, 2019, 5 pages.

U.S. Appl. No. 17/269,198—The International Bureau of WIPO, International Preliminary Report on Patentability issued in International Application PCT/US2019/046912, Feb. 23, 2021, 6 pages.

Der-Zen Liu, et al., "Immonbilized Zinc Affinity Chromatography of Pectin Hydroxamic Acids for Purification of Trypsin Inhibitors from Soybean and Sweet Potato, " Journal of Agricultural and Food Chemisty, 2005, vol. 53, No. 26, pp. 10219-10223.

U.S. Appl. No. 17/269,198—Notice of Reasons For Refusal mailed Aug. 15, 2023, issued in corresponding Japanese Application No. 2021-507751, filed Aug. 16, 2019, 7 pages.

U.S. Appl. No. 17/269,198—Office Action mailed Jun. 25, 2024, issued in corresponding Chinese Application No. 2019800654586, filed Aug. 16, 2019, 12 pages.

Fischer, M. et al., Efficacy Assessment of Nucleic Acid Decontamination Reagents Used in Molecular Diagnostics Laboratories, PLOS One, Jul. 13, 2016.

Gerba, C.P. et al., Microbiological Hazards of Household Toilets: Droplet Production and the Fate of Residual Organisms, Applied Microbiology, vol. 30, No. 2, pp. 229-237, Aug. 1975.

Gibbons, S.M. et al., Ecological Succession and Viability of Human-Associated Microbiota on Restoom Surfaces, Applied and Enviromental Microbiology, vol. 81, No. 2, pp. 765-773, Jan. 2015.

* cited by examiner

SEQUENCE LISTING

<160> NUMBER OF SEQ ID NOS: 15

<210> SEQ ID NO 1
<211> LENGTH: 16
<212> TYPE: DNA
<213> ORGANISM: Artificial sequence
<220> FEATURE:
<223> OTHER INFORMATION: Synthetic

<400> SEQUENCE: 1
ggccatcagc gcatgc                                                    16

<210> SEQ ID NO 2
<211> LENGTH: 17
<212> TYPE: DNA
<213> ORGANISM: Artificial sequence
<220> FEATURE:
<223> OTHER INFORMATION: Synthetic

<400> SEQUENCE: 2
cggctgcgag caaaaca                                                   17

<210> SEQ ID NO 3
<211> LENGTH: 27
<212> TYPE: DNA
<213> ORGANISM: Artificial sequence
<220> FEATURE:
<223> OTHER INFORMATION: Synthetic

<400> SEQUENCE: 3
cctctgccga tccatactgc ggaactc                                        27

```
<210> SEQ ID NO 4
<211> LENGTH: 20
<212> TYPE: DNA
<213> ORGANISM: Artificial sequence
<220> FEATURE:
<223> OTHER INFORMATION: Synthetic

<400> SEQUENCE: 4
aatccccaaa gtcaaggagt                                               20

<210> SEQ ID NO 5
<211> LENGTH: 17
<212> TYPE: DNA
<213> ORGANISM: Artificial sequence
<220> FEATURE:
<223> OTHER INFORMATION: Synthetic

<400> SEQUENCE: 5
actgtacccc ccaatcc                                                  17

<210> SEQ ID NO 6
<211> LENGTH: 29
<212> TYPE: DNA
<213> ORGANISM: Artificial sequence
<220> FEATURE:
<223> OTHER INFORMATION: Synthetic

<400> SEQUENCE: 6
catcttaaga cagcagtaca aatggcagt                                     29

<210> SEQ ID NO 7
<211> LENGTH: 13
<212> TYPE: DNA
<213> ORGANISM: Artificial sequence
<220> FEATURE:
<223> OTHER INFORMATION: Synthetic

<400> SEQUENCE: 7
gaaacaccgc ccg                                                      13

<210> SEQ ID NO 8
<211> LENGTH: 21
<212> TYPE: DNA
<213> ORGANISM: Artificial sequence
<220> FEATURE:
<223> OTHER INFORMATION: Synthetic

<400> SEQUENCE: 8
tttgaccggt taaaaaaaga t                                             21

<210> SEQ ID NO 9
<211> LENGTH: 21
<212> TYPE: DNA
<213> ORGANISM: Artificial sequence
<220> FEATURE:
<223> OTHER INFORMATION: Synthetic

<400> SEQUENCE: 9
ccgcccttca acatcagtga a                                             21
```

<210> SEQ ID NO 10
<211> LENGTH: 19
<212> TYPE: DNA
<213> ORGANISM: Artificial sequence
<220> FEATURE:
<223> OTHER INFORMATION: Synthetic

<400> SEQUENCE: 10
acgcatgctg atagcgtca                                              19

<210> SEQ ID NO 11
<211> LENGTH: 20
<212> TYPE: DNA
<213> ORGANISM: Artificial sequence
<220> FEATURE:
<223> OTHER INFORMATION: Synthetic

<400> SEQUENCE: 11
tgagttctgc ttcctccttg                                             20

<210> SEQ ID NO 12
<211> LENGTH: 26
<212> TYPE: DNA
<213> ORGANISM: Artificial sequence
<220> FEATURE:
<223> OTHER INFORMATION: Synthetic

<400> SEQUENCE: 12
ccggagatcc ttgcgatcct tgcacc                                      26

<210> SEQ ID NO 13
<211> LENGTH: 21
<212> TYPE: DNA
<213> ORGANISM: Artificial sequence
<220> FEATURE:
<223> OTHER INFORMATION: Synthetic

<400> SEQUENCE: 13
gcattcctga agctgacagc a                                           21

<210> SEQ ID NO 14
<211> LENGTH: 24
<212> TYPE: DNA
<213> ORGANISM: Artificial sequence
<220> FEATURE:
<223> OTHER INFORMATION: Synthetic

<400> SEQUENCE: 14
ctccaggcca gaaagagaga gtag                                        24

<210> SEQ ID NO 15
<211> LENGTH: 22
<212> TYPE: DNA
<213> ORGANISM: Artificial sequence
<220> FEATURE:
<223> OTHER INFORMATION: Synthetic

<400> SEQUENCE: 15
ccgtggcctt agctgtgctc gc                                          22

METHODS AND COMPOSITIONS FOR NUCLEIC ACID ISOLATION

CROSS-REFERENCE(S) TO RELATED APPLICATION(S)

This application claims the benefit of U.S. Provisional Application No. 62/765,013, filed Aug. 17, 2018, which is incorporated herein by reference in its entirety.

STATEMENT REGARDING SEQUENCE LISTING

The sequence listing associated with this application is provided in text format in lieu of a paper copy and is hereby incorporated by reference into the specification. The name of the text file containing the sequence listing is 70132_Seq_Final_2019-08-14.txt. The text file is 3.0 KB; was created on Aug. 14, 2019; and is being submitted via EFS-Web with the filing of the specification.

FIELD OF THE INVENTION

The invention relates to methods and compositions for isolation of nucleic acids from nucleic acid-containing samples.

BACKGROUND

Molecular diagnostic assays that utilize amplification and/or detection of nucleic acids by various automated analytical techniques, such as polymerase chain reaction (PCR), provide rapid and accurate results in less time compared to traditional diagnostic methods and can be easily automated. However, in order to perform molecular diagnostic analysis of biological samples, nucleic acids have to be isolated from the biological materials to remove components that can affect the accuracy of the assay, e.g., by inhibiting the polymerase activity. Even though a variety of methods for nucleic acid extraction exists, currently available methods generally involve lengthy steps and are not easily amenable to automation. Thus, preparation of nucleic acid samples prior to amplification and detection of specific targets is the most challenging step of molecular diagnostics.

Simple and rapid methods of nucleic acid isolation that do not require extensive sample processing and that can be adapted to clinical laboratory automation are needed for producing quality nucleic acids free of inhibitors of amplification. There is a need for agents that can facilitate isolation of nucleic acids from nucleic acid-containing biological samples in a manner compatible with fast, automated nucleic acid detection methods.

SUMMARY

In one aspect, provided herein is a method for isolation of a nucleic acid from a sample comprising a nucleic acid, comprising:
(a) contacting a sample comprising a nucleic acid with an aqueous composition comprising a polysaccharide comprising one or more uronic acid units acid units; and
(b) concentrating the nucleic acid on a solid support thereby isolating the nucleic acid.

In some embodiments of the methods disclosed herein, the polysaccharide further comprises a modified uronic acid unit such as an uronic acid amide unit, uronic acid ester unit, or a combination thereof.

In some embodiments, the polysaccharide further comprises one or more units represented by Formula II:

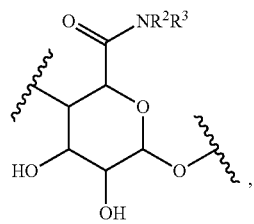

an isomer, a salt, a tautomer, or a combination thereof, wherein:

$R^2$ and $R^3$ are independently H, optionally substituted C1-C8 alkyl, optionally substituted C3-C8 cycloalkyl, optionally substituted C3-C8 heterocycloalkyl, or optionally substituted C2-C20 heteroalkyl.

In some embodiments, the polysaccharide further comprises one or more units of Formula (III):

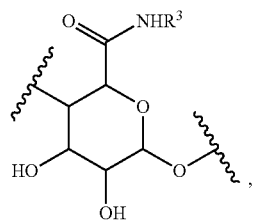

an isomer, a salt, a tautomer, or a combination thereof, wherein $R^3$ is $CH_2CH_2NH_2$, $CH_2CH_2N(CH_3)_2$, $CH_2CH_2OH$, $NH_2$, H, $CH_3$, $CH_2CH_2OCH_2CH_2NH_2$, or $CH_2CH_2NHCH_2CH_2NH_2$.

In some embodiments, the polysaccharide comprises one or more monomeric units having the structure of Formula VI:

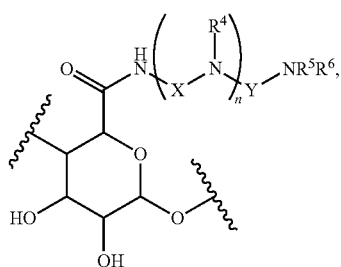

an isomer, a salt, a tautomer, or a combination thereof, wherein:

n is 0, 1, 2, or 3;

$R^4$ is H or C1-C3 alkyl;

X, at each occurrence, is independently C2-C4 alkylene or C4-C6 heteroalkylene;

Y is a C2-C3 alkylene or C4-C6 heteroalkylene; and $R^5$ and $R^6$ are independently H or C1-C3 alkyl.

In some embodiments, the polysaccharide comprises one or more monomeric units having the structure of Formula V:

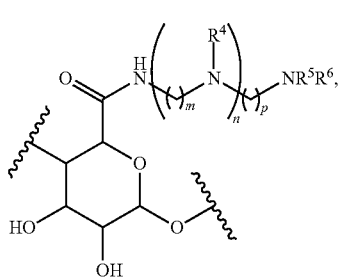
(V)

an isomer, a salt, a tautomer, or a combination thereof, wherein:
n is 0, 1, 2, or 3;
m, at each occurrence, is independently 2, 3, or 4;
p is 2, 3, or 4;
$R^1$, $R^2$, and $R^3$ are independently H or C1-C3 alkyl;
$R^4$ is H or C1-C3 alkyl; and
$R^5$ and $R^6$ are independently H or C1-C3 alkyl.

In some embodiments, the polysaccharide comprises one or more units represented by Formula VI, Formula VII, or Formula VIII:

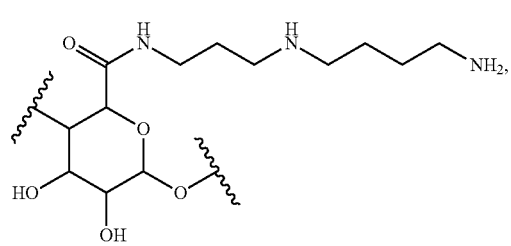
(VI)

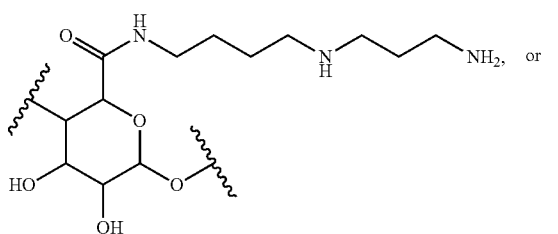
(VII)

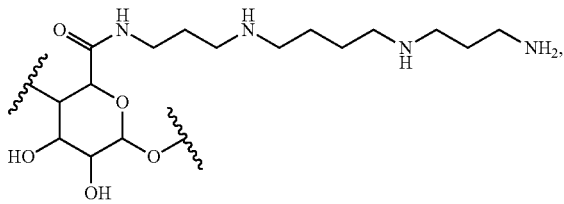
(VIII)

their isomers, salts, tautomers, or combinations thereof.

In some embodiments, the polysaccharide is a water-soluble polysaccharide.

In some embodiments, the polysaccharide is a modified pectin. In some embodiments, the modified pectin is selected from partially de-esterified pectin, partially de-esterified depolymerized pectin, amidated pectin, amidated depolymerized pectin, or mixtures thereof. In some embodiments, the modified pectin is a modified citrus pectin or a modified apple pectin.

In some embodiments, the polysaccharide is present in the aqueous composition at a concentration of about 0.1 µg/mL to about 1000 µg/mL, about 0.1 µg/mL to about 500 µg/mL, about 0.1 µg/mL to about 200 µg/mL, about 0.1 µg/mL to about 100 µg/mL, about 0.1 µg/mL to about 50 µg/mL, about 0.1 µg/mL to about 20 µg/mL, about 1 µg/mL to about 200 µg/mL, about 1 µg/mL to about 100 µg/mL, about 1 µg/mL to about 50 µg/mL, or from about 1 µg to about 20 µg.

In some embodiments, the polysaccharide has a relative molecular weight between about 120 kDa and about 500 kDa, between about 150 kDa and about 300 kDa, or between about 120 kDa and about 175 kDa. In some embodiments, the modified pectin is obtained by amidation of an unmodified pectin. In some embodiments, the unmodified pectin has a relative molecular weight between between about 5 kDa and about 1,100 kDa, between about 10 kDa and about 500 kDa, between about 10 kDa and about 300 kDa, between about 20 kDa and about 200 kDa, or between about 20 kDa and about 100 kDa.

In some embodiments, the nucleic acid is concentrated on a solid support by centrifugation, precipitation, or a combination thereof. In some embodiments, the nucleic acid is concentrated by precipitation on a solid support, for example, by centrifugation or by passing through a filter.

In some embodiments, the solid support comprises a material selected from silica, glass, ethylenic backbone polymer, mica, polycarbonate, zeolite, titanium dioxide, or a combination thereof. In some embodiments, the solid support is a magnetic bead, glass bead, cellulose filter, polycarbonate filter, polytetrafluoroethylene filter, polyvinylpyrrolidone filter, polyethersulfone filter, or glass filter. In some embodiments, the solid support is a wall of a centrifuge tube such as polyethylene or polypropylene tube.

In some embodiments, the method further comprises washing the nucleic acid precipitated or concentrated on the solid support.

In some embodiments, the method further comprises eluting the nucleic acid from the solid support. In some embodiments, the method further comprises washing and eluting steps.

In some embodiments, eluting the nucleic acid comprises contacting the concentrated nucleic acid with an eluting agent. In some embodiments, the eluting agent comprises ammonia or an alkali metal hydroxide. In some embodiments, the eluting agent has a pH of above about 9, above about 10, or above about 11. In some embodiments, the eluting agent has a pH of about 9 to about 12, about 9.5 to about 12, about 10 to about 12, or about 9 to about 11. In some embodiments, the eluting agent comprises a polyanion. In some embodiments, the polyanion is a carrageenan. In some embodiments, the polyanion is a carrier nucleic acid. In some embodiments, the eluting agent comprises carrageenan and alkali metal hydroxide or ammonium hydroxide. In some embodiments, the carrageenan is i-carrageenan. In some embodiments, the eluting agent comprises i-carrageenan and potassium hydroxide.

In some embodiments, the aqueous composition further comprises a lysis agent. In some embodiments, the aqueous composition further comprises a chaotropic agent. In some embodiments, the chaotropic agent is selected from guanidinium thiocyanate, guanidinium hydrochloride, alkali perchlorate, alkali iodide, urea, formamide, or combinations thereof. In some embodiments, the aqueous solution further comprises a salt. In some embodiments, the salt is sodium chloride or calcium chloride. In some embodiments, the aqueous composition further comprises a buffering agent. In some embodiments, the buffering agent is Tris or HEPES. In some embodiments, the aqueous composition further comprises a surfactant. In some embodiments, the surfactant is a polysorbate. In some embodiments, the aqueous composition further comprises a defoaming agent.

In some embodiments, the sample is blood, plasma, serum, semen, tissue biopsy, tear, urine, stool, saliva, spinal fluid, smear preparation, bacterial culture, mammalian cell culture, viral culture, human cell, bacteria, extracellular fluid, PCR reaction mixture, or in vitro nucleic acid modification reaction mixture. In some embodiments, the tissue biopsy is a paraffin-embedded tissue. In some embodiments, the nucleic acid comprises genomic DNA. In some embodiments, the nucleic acid comprises total RNA. In some embodiments, the sample comprises microbial nucleic acid or viral nucleic acid. In some embodiments, the viral nucleic acid is HBV DNA. In some embodiments, the nucleic acid comprises circulating nucleic acid.

In some embodiments, the method is performed in a cartridge.

In some embodiments, the sample is a cell lysate. In some embodiments, the sample is contacted with a lysis buffer prior to contacting with the aqueous composition. In some embodiments, the lysis buffer comprises one or more proteases.

In another aspect, provided herein is a method for detecting a nucleic acid in a sample, comprising:

(a) contacting the sample with an aqueous composition comprising a polysaccharide comprising one or more uronic acid units;

(b) concentrating the nucleic acid; and (c) detecting the nucleic acid.

In some embodiments, the polysaccharide comprises one or more units represented by Formula II:

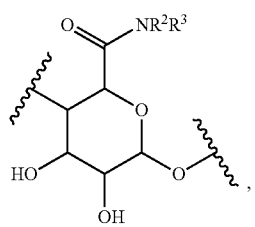

(II)

an isomer, a salt, a tautomer, or a combination thereof, wherein $R^2$ and $R^3$ are independently selected from H, optionally substituted C1-C8 alkyl, optionally substituted C3-C8 cycloalkyl, optionally substituted C3-C8 heterocycloalkyl, and optionally substituted C2-C20 heteroalkyl.

In some embodiments, the polysaccharide further comprises one or more units represented by Formula III:

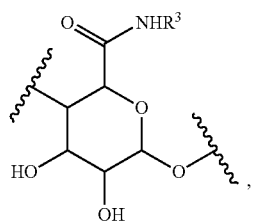

(III)

an isomer, a salt, a tautomer, or a combination thereof, wherein $R^3$ is H, $CH_2CH_2NH_2$, $CH_2CH_2N(CH_3)_2$, $CH_2CH_2OH$, $NH_2$, $NCH_3$, $CH_2CH_2OCH_2CH_2NH_2$, or $CH_2CH_2NHCH_2CH_2NH_2$.

In some embodiments, the polysaccharide comprises one or more monomeric units represented by Formula VI:

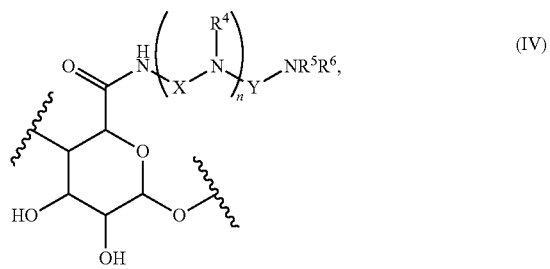

(IV)

an isomer, a salt, a tautomer, or a combination thereof, wherein:

n is 0, 1, 2, or 3;

$R^4$ is H or C1-C3 alkyl;

X, at each occurrence, is independently C2-C4 alkylene or C4-C6 heteroalkylene;

Y is a C2-C3 alkylene or C4-C6 heteroalkylene; and $R^5$ and $R^6$ are independently H or C1-C3 alkyl.

In some embodiments, the polysaccharide comprises one or more monomeric units represented by Formula V:

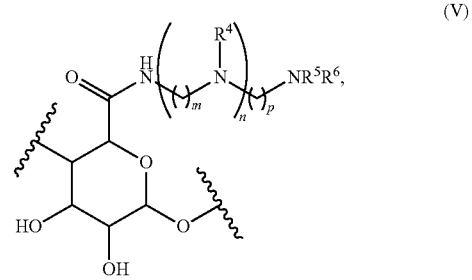

(V)

an isomer, a salt, a tautomer, or a combination thereof, wherein:

n is 0, 1, 2, or 3;

m, at each occurrence, is independently 2, 3, or 4;

p is 2, 3, or 4;

$R^4$ is H or C1-C3 alkyl; and $R^5$ and $R^6$ are independently H or C1-C3 alkyl.

In some embodiments, the polysaccharide comprises one or more monomeric units represented by Formula VI, Formula VII, or Formula VIII:

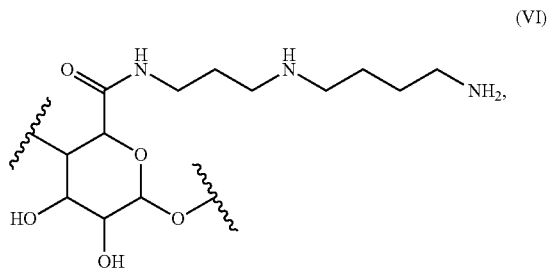

(VI)

-continued

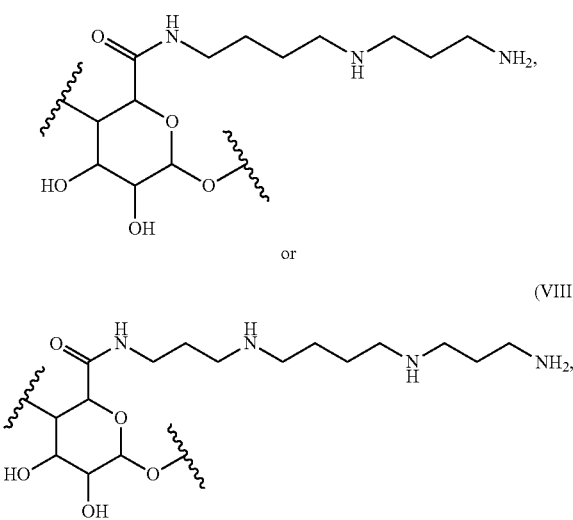

their isomers, salts, tautomers, or combinations thereof.

In some embodiments, the polysaccharide is a modified pectin. In some embodiments, the modified pectin is a modified citrus pectin or modified apple pectin.

In some embodiments, the polysaccharide is present in the aqueous composition at a concentration of about 0.1 µg/mL to about 1000 µg/mL, about 0.1 µg/mL to about 500 µg/mL, about 0.1 µg/mL to about 200 µg/mL, about 0.1 µg/mL to about 100 µg/mL, about 0.1 µg/mL to about 50 µg/mL, about 0.1 µg/mL to about 20 µg/mL, about 1 µg/mL to about 200 µg/mL, about 1 µg/mL to about 100 µg/mL, about 1 µg/mL to about 50 µg/mL, or from about 1 µg to about 20 µg.

In some embodiments, detecting the nucleic acid comprises amplifying the nucleic acid by polymerase chain reaction.

In some embodiments, the polymerase chain reaction is a nested PCR, an isothermal PCR, qPCR, or RT-PCR.

In another aspect, provided herein a kit for nucleic acid isolation comprising a polysaccharide comprising one or more units represented by Formulae (II)-(VIII). In some embodiments, the kit comprises instructions for use. In some embodiments, the kit comprises a solution of a polysaccharide comprising one or more units represented by Formulae (I)-(VIII). In some embodiments, the kit comprises a polysaccharide comprising one or more units represented by Formulae (I)-(VIII) in solid form. In some embodiments, the kit further comprises a cell lysis reagent or a cell lysis component. In some embodiments, the kit further comprises an elution reagent. In some embodiments, the kit further comprises a buffer component. In some embodiments, the kit further comprises a salt. In some embodiments, the kit further comprises a chaotropic agent component.

DETAILED DESCRIPTION

Provided herein are methods for isolation of nucleic acids from nucleic acid-containing samples in a manner compatible with automated nucleic acid amplification assays.

In one aspect, provided herein are methods for isolation of nucleic acids from nucleic-acid containing samples comprising contacting a nucleic acid-containing sample with an aqueous composition, wherein the aqueous composition comprises a polysaccharide comprising one or more uronic acid units, to provide isolated (e.g., precipitated or concentrated) nucleic acid.

The compositions and methods described herein can be used to isolate, for example, concentrate or precipitate nucleic acids from a variety of nucleic acid-containing samples. Suitable samples include blood, plasma, serum, semen, tissue biopsy, urine, stool, saliva, smear preparation, paraffin-embedded tissue, bacterial culture, cell culture, viral culture, PCR reaction mixtures, and in vitro nucleic acid modification reaction mixtures, and mixtures thereof.

A technical feature of the methods of the present invention is the use of a polysaccharide comprising one or more uronic acid units to facilitate isolation, e.g., by precipitation or flocculation, of nucleic acids from samples such as cell lysates and tissue. The inventors discovered that some polysaccharide agents disclosed herein, when added to nucleic acid-containing samples, such as cell lysates and other biological samples, at concentrations ranging from about 0.1 µg/mL to about 1,000 µg/mL surprisingly facilitate recovery of the nucleic acids by conventional methods such as centrifugation or filtration through a porous substrate with increased yields. In some embodiments, the methods allow isolation of nucleic acids at room temperature which makes the methods useful for automated, cartridge-based molecular diagnostics assays. Moreover, the methods do not require removal of the polysaccharide agents from the isolated nucleic acids or additional purification steps because presence of the agents does not inhibit detection of the isolated nucleic acids by standard nucleic acid amplification methods, such as PCR.

Polysaccharide Agents

In some embodiments, the polysaccharide agents described herein comprise one or more uronic acid units. In some embodiments, the polysaccharide agents comprise uronic acid monomeric units. Preferably, the polysaccharide comprises one or more galacturonic acid units. In some embodiments, the polysaccharide agent is a polygalacturonic acid (PGA). In other embodiments, the polysaccharide is gellan gum, oxidized starch, oxidized cellulose, oxidized dextran, and combinations thereof.

In some embodiments, the polysaccharide comprises a plurality of uronic acid units and one or more additional monomeric units. Uronic acids include sugar acids comprising both carbonyl (e.g., aldehyde or keto group) and carboxylic acid (—COOH) functional groups. Typically, uronic acids are derived from sugars in which the terminal hydroxyl group has been oxidized to a carboxylic acid and are generally named according to their parent sugars, for example, a glucuronic acid is the uronic acid derived from glucose. Uronic acids derived from hexoses are known as hexuronic acids, and uronic acids derived from pentoses are known as penturonic acids.

In some embodiments, in addition to one or more uronic acid units, the polysaccharide agents further comprise one or more additional units selected from the group consisting of units represented by Formula (I) or Formula (II):

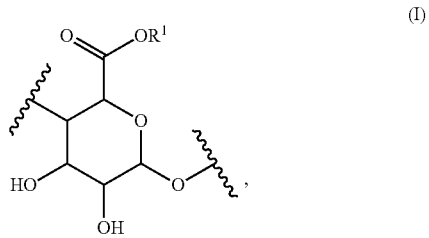

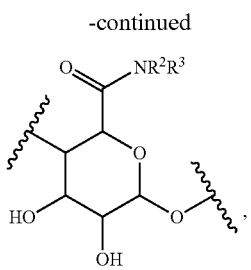

(II)

or an isomer, a salt, a tautomer, or a combination thereof, wherein $R^1$ is selected from optionally substituted $C_1$-$C_8$ alkyl, optionally substituted $C_3$-$C_8$ cycloalkyl, optionally substituted $C_3$-$C_8$ heterocycloalkyl, and optionally substituted $C_2$-$C_{20}$ heteroalkyl; and $R^2$ and $R^3$ are independently selected from H, optionally substituted $C_1$-$C_6$ alkyl, optionally substituted $C_3$-$C_6$ cycloalkyl, and optionally substituted $C_4$-$C_{20}$ heteroalkyl.

In some embodiments, $R^3$ is an optionally substituted $C_1$-$C_6$ alkyl. In some embodiments, $R^3$ is an optionally substituted $C_4$-$C_{20}$ heteroalkyl, for example, an short PEG chain optionally substituted with one or more amino groups.

In some embodiments, each of $R^1$, $R^2$, and $R^3$ comprises no more than one amino group. In some embodiments, each of $R^1$, $R^2$, and $R^3$ does not comprise an amino group. In some embodiments, each of $R^2$ and $R^3$ comprise one or more amino groups. In some embodiments, $R^2$ is H and $R^3$ is a $C_4$-$C_{20}$ heteroalkyl, for example, a polyamine or an oligomeric ethylene glycol comprising 2-6 ethylene glycol units.

In some embodiments, $R^1$ is methyl, ethyl, or propyl. In some embodiments, $R^2$ and $R^3$ are both H. In some embodiments, $R^2$ is H and $R^3$ is an optionally substituted $C_1$-$C_8$ alkyl. In some embodiments, $R^2$ is H and $R^3$ is $CH_2CH_2NH_2$, $CH_2CH_2N(CH_3)_2$, $CH_2CH_2NHCH_2CH_2NH_2$, $CH_2CH_2OH$, $NH_2$, H, or $CH_3$. In some embodiments, both $R^2$ and $R^3$ are $CH_3$.

As used herein, the terms "alkyl," "alkenyl," and "alkynyl" include straight-chain, branched-chain, and cyclic monovalent hydrocarbyl radicals, and combinations thereof, which contain only C and H when they are unsubstituted. Examples include methyl, ethyl, isobutyl, cyclohexyl, cyclopentylethyl, 2-propenyl, 3-butynyl, and the like. The total number of carbon atoms in each such group is sometimes described herein, e.g., when the group can contain up to ten carbon atoms, it can be represented as 1-10 C, C1-C10, $C_1$-$C_{10}$, $C_{1-10}$, or C1-10. The term "heteroalkyl," "heteroalkenyl," and "heteroalkynyl," as used herein, mean the corresponding hydrocarbons wherein one or more chain carbon atoms have been replaced by a heteroatom. Exemplary heteroatoms include N, O, S, and P. When heteroatoms are allowed to replace carbon atoms, for example, in heteroalkyl groups, the numbers describing the group, though still written as e.g. C3-C10, represent the sum of the number of carbon atoms in the cycle or chain plus the number of such heteroatoms that are included as replacements for carbon atoms in the cycle or chain being described.

A single group can include more than one type of multiple bond, or more than one multiple bond; such groups are included within the definition of the term "alkenyl" when they contain at least one carbon-carbon double bond, and are included within the term "alkynyl" when they contain at least one carbon-carbon triple bond.

Alkyl, alkenyl, and alkynyl groups can be optionally substituted to the extent that such substitution makes sense chemically. Typical substituents include, but are not limited to, halogens (F, Cl, Br, I), =O, =NCN, =NOR, =NR, OR, $NR_2$, SR, $SO_2R$, $SO_2NR_2$, $NRSO_2R$, $NRCONR_2$, NRC(O) OR, NRC(O)R, CN, C(O)OR, $C(O)NR_2$, OC(O)R, C(O)R, and $NO_2$, wherein each R is independently H, C1-C8 alkyl, C2-C8 heteroalkyl, C1-C8 acyl, C2-C8 heteroacyl, C2-C8 alkenyl, C2-C8 heteroalkenyl, C2-C8 alkynyl, C2-C8 heteroalkynyl, C6-C10 aryl, or C5-C10 heteroaryl, and each R is optionally substituted with halogens (F, Cl, Br, I), =O, =NCN, =NOR', =NR', OR', NR'$_2$, SR', $SO_2$R', $SO_2$NR'$_2$, NR'$SO_2$R', NR'CONR'$_2$, NR'C(O)OR', NR'C(O)R', CN, C(O)OR', C(O)NR'$_2$, OC(O)R', C(O)R', and $NO_2$, wherein each R' is independently H, C1-C8 alkyl, C2-C8 heteroalkyl, C1-C8 acyl, C2-C8 heteroacyl, C6-C10 aryl or C5-C10 heteroaryl. Alkyl, alkenyl, and alkynyl groups can also be substituted by C1-C8 acyl, C2-C8 heteroacyl, C6-C10 aryl or C5-C10 heteroaryl, each of which can be substituted by the substituents that are appropriate for the particular group.

While "alkyl" as used herein includes cycloalkyl and cycloalkylalkyl groups, the term "cycloalkyl" is used herein to describe a carbocyclic non-aromatic group that is connected via a ring carbon atom, and "cycloalkylalkyl" is used to describe a carbocyclic non-aromatic group that is connected to the molecule through an alkyl linker. Similarly, "heterocyclyl" is used to identify a non-aromatic cyclic group that contains at least one heteroatom as a ring member and that is connected to the molecule via a ring atom, which may be C or N; and "heterocyclylalkyl" can be used to describe such a group that is connected to another molecule through an alkylene linker. As used herein, these terms also include rings that contain a double bond or two, as long as the ring is not aromatic.

"Aromatic" or "aryl" substituent or moiety refers to a monocyclic or fused bicyclic moiety having the well-known characteristics of aromaticity; examples of aryls include phenyl and naphthyl. Similarly, "heteroaromatic" and "heteroaryl" refer to such monocyclic or fused bicyclic ring systems which contain as ring members one or more heteroatoms. Suitable heteroatoms include N, O, and S, inclusion of which permits aromaticity in 5-membered rings as well as 6-membered rings. Typical heteroaromatic systems include monocyclic C5-C6 aromatic groups such as pyridyl, pyrimidyl, pyrazinyl, thienyl, furanyl, pyrrolyl, pyrazolyl, thiazolyl, oxazolyl, and imidazolyl, and fused bicyclic moieties formed by fusing one of these monocyclic groups with a phenyl ring or with any of the heteroaromatic monocyclic groups to form a C8-C10 bicyclic group such as indolyl, benzimidazolyl, indazolyl, benzotriazolyl, isoquinolyl, quinolyl, benzothiazolyl, benzofuranyl, pyrazolopyridyl, quinazolinyl, quinoxalinyl, cinnolinyl, and the like. Any monocyclic or fused ring bicyclic system which has the characteristics of aromaticity in terms of electron distribution throughout the ring system is included in this definition. It also includes bicyclic groups where at least the ring which is directly attached to the remainder of the molecule has the characteristics of aromaticity. Typically, the ring systems contain 5-14 ring member atoms. Typically, monocyclic heteroaryls contain 5-6 ring members, and bicyclic heteroaryls contain 8-10 ring members.

Aryl and heteroaryl moieties can be substituted with a variety of substituents including C1-C8 alkyl, C2-C8 alkenyl, C2-C8 alkynyl, C5-C12 aryl, C1-C8 acyl, and heteroforms of these, each of which can itself be further substituted; other substituents for aryl and heteroaryl moieties include halogens (F, Cl, Br, I), OR, $NR_2$, SR, $SO_2R$, $SO_2NR_2$, $NRSO_2R$, $NRCONR_2$, NRC(O)OR, NRC(O)R, CN, C(O)OR, $C(O)NR_2$, OC(O)R, C(O)R, and $NO_2$, wherein each R is independently H, C1-C8 alkyl, C2-C8 heteroalkyl, C2-C8 alkenyl, C2-C8 heteroalkenyl, C2-C8 alkynyl, C2-C8 heteroalkynyl, C6-C10 aryl, C5-C10 heteroaryl, C7-C12 arylalkyl, or C6-C12 heteroarylalkyl, and each R is optionally substituted as described above for alkyl groups. The substituent groups on an aryl or heteroaryl group can be further substituted with the groups described herein as suitable for each type of such substituents or for each component of the substituent. Thus, for example, an arylalkyl substituent can be substituted on the aryl portion with substituents described herein as typical for aryl groups, and it can be further substituted on the alkyl portion with substituents described herein as typical or suitable for alkyl groups.

"Optionally substituted," as used herein, indicates that the particular group being described can have one or more hydrogen substituents replaced by a non-hydrogen substituent. In some optionally substituted groups or moieties, all hydrogen substituents are replaced by a non-hydrogen substituent (e.g., a polyfluorinated alkyl such as trifluoromethyl). If not otherwise specified, the total number of such substituents that can be present is equal to the number of H atoms present on the unsubstituted form of the group being described. Where an optional substituent is attached via a double bond, such as a carbonyl oxygen or oxo (=O), the group takes up two available valences, so the total number of substituents that may be included is reduced according to the number of available valences.

In some embodiments, the polysaccharide agents further comprise one or more units of Formula (III):

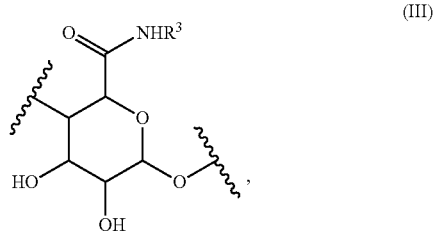

(III)

or an isomer, a salt, a tautomer, or a combination thereof, wherein:

$R^3$ is $CH_2CH_2NH_2$, $CH_2CH_2N(CH_3)_2$, $CH_2CH_2OH$, $CH_3$, $(CH_2)_2O(CH_2)_2NH_2$, or $CH_2CH_2NHCH_2CH_2NH_2$. In some embodiments, $R^3$ is H. In some embodiments, $R^3$ is $CH_2CH_2OH$.

It is understood that if a polysaccharide comprises two or more units of Formula (II) or (III), their $R^3$ can be the same or different within the polysaccharide.

In some embodiments, the polysaccharide agent is a modified pectin. Pectins are naturally occurring complex polysaccharides typically found in plant cell walls. Pectins typically comprise an alpha 1-4 linked polygalacturonic acid backbone intervened by rhamnose residues and modified with neutral sugar side chains and non-sugar components such as acetyl, methyl, and ferulic acid groups. The galacturonic acid residues in pectin are partly esterified and present as the methyl esters. Pectins are typically characterized by their degree of esterification, which is defined as the percentage of carboxyl groups esterified. Pectins with a degree of esterification, e.g., above 50%, are classified as high methyl ester ("HM") pectins or high ester pectins, and pectins with a degree of esterification lower than 50% are referred to as low methyl ester ("LM") pectins or low ester pectins. Most pectins found in fruits and vegetables are HM pectins. In some embodiments of the methods disclosed herein, the polysaccharide agents are HM pectins or modified HM pectins.

As used herein, the term "modified pectin" refers to any naturally occurring pectin that has been structurally modified, e.g., by chemical, physical, or biological (including enzymatic) means, or by some combination thereof. Non-limiting examples of such modification to the pectin structure include de-esterification, hydrolysis, oxidation and/or reduction of sugar moieties, functionalization of sugar moieties, conformational changes, and changes in molecular weight, linkage, and states of aggregation. In some embodiments, the structural modification includes de-esterification and hydrolysis. In other embodiments, the structural modification includes reduction in molecular weight and/or degree of polymerization.

Modified pectins can be produced by chemical means known in the art, including any chemical reaction or process that disrupts or changes chemical bonds of the pectin structure, such as covalent or ionic bonds. By way of example, chemical bonding may be disrupted or formed by catalysis, hydrolysis, aminolysis, substitution, elimination, reduction, oxidation, and radical reactions. In some embodiments, modified pectin is produced by a process that includes hydrolysis, which is preferably catalyzed, e.g., by an acid or base.

In some embodiments, the modified pectin is an amidated pectin. Amidated pectins can be prepared by methods known in the art. For example, a pectin comprising ester groups, such as an unmodified pectin, can be contacted with a solution of a suitable amine thereby converting the ester groups of the unmodified pectin to amides, for example, as shown in Scheme 1.

Scheme 1

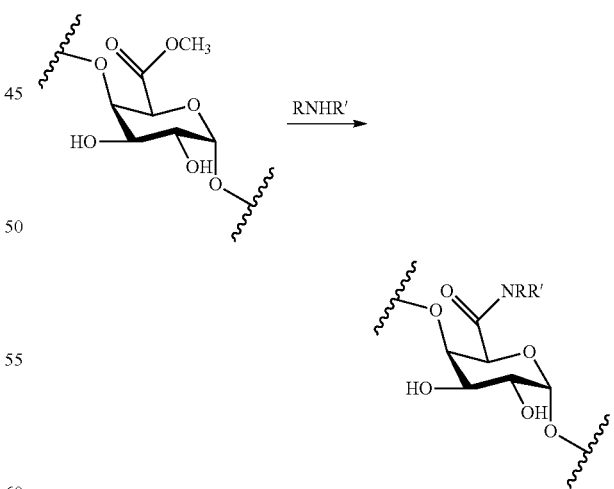

Alternatively, unmodified pectin or pectin in which all or some of the ester groups have been hydrolyzed can be reacted with a primary or a secondary amine or a mixture of amines in the presence of a suitable coupling agent to form amidated pectin, as depicted in Scheme 2.

Scheme 2

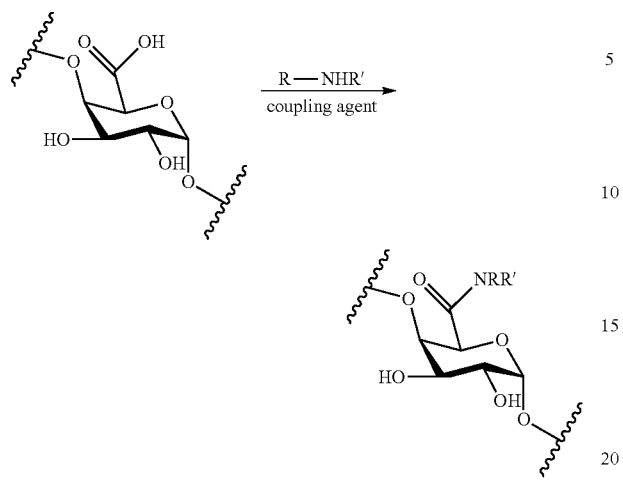

Any suitable coupling method and reagent can be used to prepare amidated pectins disclosed herein. Non-limiting examples of suitable coupling agents include carbodiimide coupling agents such as DCC and EDCI, and phosphonium and imonium type reagents such as BOP, PyBOP, PyBrOP, TBTU, HBTU, HATU, COMU, and TFFH.

In some embodiments, the polysaccharide reagents disclosed herein can be obtained by reductive amination of a periodate-treated polysaccharide, e.g., pectin. Methods of reductive amination of such polysaccharides are known in the art.

A modified, e.g., amidated pectin can be obtained by any of the methods described herein. Particularly useful starting materials for synthesis of modified pectins include fruit pectins, for example, apple and citrus pectins. In some embodiments, the precursor (unmodified) pectins have relative molecular weights between about 5 kDa and about 1,100 kDa, between about 10 kDa and about 500 kDa, between about 10 kDa and about 300 kDa, between about 20 kDa and about 200 kDa, or between about 20 kDa and about 100 kDa. In some embodiments, the polysaccharide agents have relative molecular weights between about 120 kDa and about 300 kDa, between about 150 kDa and about 300 kDa, or between about 120 kDa and about 175 kDa. In some embodiments, the relative molecular weights of the amidated pectins can be determined by size exclusion chromatography using a molecular weight standard, such as Pullulan series standards, as a reference.

In some embodiments, the modified pectin is a compound of Table 2.

In some embodiments, the amidated pectin is a pectin amidated with ammonia. In some embodiments, the amidated pectin is a pectin amidated with aminoethanol. In other embodiments, the amidated pectin is a pectin amidated with ethylene diamine. In other embodiments, the amidated pectin is a pectin amidated with diethylene triamine. In some embodiments, the amidated pectin comprises one or more units represented by Formula (II) or Formula (III). In some embodiments, the amidated pectin is a pectin obtained by by any of the procedures A-L listed in the Table 1 below.

In some embodiments, the modified pectin is a pectin that was modified by reductive amination of a periodate-oxidized pectin, for example, according to methods known in the art. Thus, in an aspect, provided herein is a method of nucleic acid isolation from a sample, comprising contacting a sample comprising a nucleic acid with an aqueous composition comprising a modified polysaccharide and concentrating the nucleic acid on a solid support thereby isolating the nucleic acid, wherein the modified polysaccharide is a pectin that was that was modified by reductive amination of a periodate-oxidized pectin. In some embodiments, the reductive amination os carried out by contacting periodate-oxidized pectin with a polyamine, e.g., spermine or spermidine, and a borohydride.

In some embodiments, the amidated pectins disclosed herein comprise one or more monomeric units having at least one amino group. In some embodiments, the amidated pectins comprise one or more monomeric units represented by Formula IV:

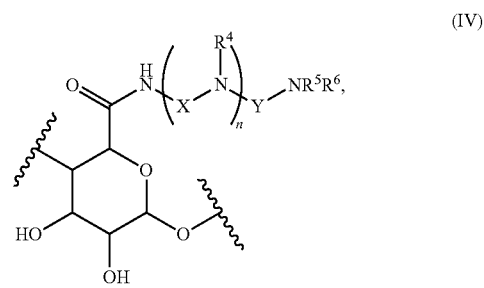

(IV)

an isomer, a salt, a tautomer, or a combination thereof, wherein:
n is 0, 1, 2 or 3;
$R^4$ is H or $C_1$-$C_3$ alkyl;
X, at each occurrence, is independently $C_2$-$C_4$ alkylene or $C_4$-$C_6$ heteroalkylene;
Y is a $C_2$-$C_3$ alkylene or $C_4$-$C_6$ heteroalkylene; and
$R^5$ and $R^6$ are independently H or $C_1$-$C_3$ alkyl.

In some embodiments, the amidated pectins disclosed herein comprise one or more monomeric units represented by Formula V:

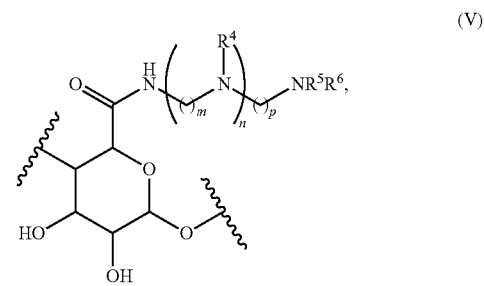

(V)

an isomer, a salt, a tautomer, or a combination thereof, wherein:
n is 0, 1, 2, or 3;
m, at each occurrence, is independently 2, 3 or 4;
p is 2, 3 or 4;
$R^4$ is H or $C_1$-$C_3$ alkyl; and
$R^5$ and $R^6$ are independently H or $C_1$-$C_3$ alkyl.

In some embodiments of the methods disclosed herein, the amidated pectin or the modified pectin comprises one or more monomeric units comprising a primary amino group. In some embodiments, the amidated pectin is amidated with a polyamine. As used herein, a polyamine is a compound comprising a plurality of amino groups, such as primary, secondary, and tertiary amino groups and combinations thereof. Polyamines suitable for modification of pectins disclosed herein include both synthetic polyamines and naturally occurring polyamines, e.g., spermidine, spermine, and putrescine. In some embodiments, the polyamine is selected from spermine, spermidine, cadaverine, ethylenediamine, and putrescine. In some embodiments, the polyamine is spermine or spermidine.

In some embodiments, the amidated pectin comprises one or more units represented the polysaccharide comprises one or more units represented by Formula VI, Formula VII, or Formula VIII:

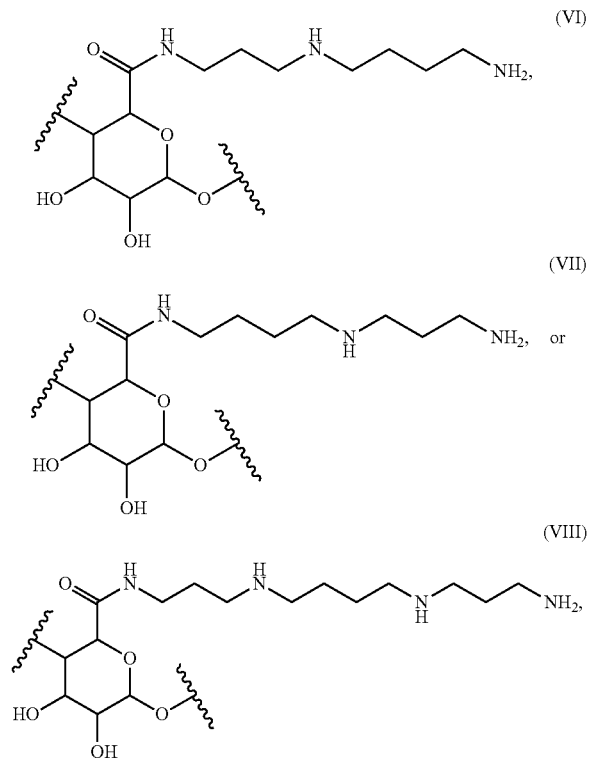

their isomers, salts, tautomers, or combinations thereof.

In some embodiments, the amidated pectins comprise a plurality of monomeric units represented by the structure of Formulae I-VII. As used herein, the term "plurality" means more than one. For example, a plurality of monomeric units means at least two monomeric units, at least three monomeric units, or at least monomeric units, and the like. If an embodiment of the present invention comprises more than one monomeric units, they may also be referred to as a first monomeric unit, a second monomeric unit, a third monomeric unit, etc.

In some embodiments, the polysaccharide agent is a water-soluble polysaccharide, for example, water-soluble modified or amidated pectin. In some embodiments, the polysaccharide is dissolved in the compositions. In some embodiments, the polysaccharide agent is dispersed in the compositions, e.g., the composition comprises a suspension of the polysaccharide agent. In some embodiments, the composition comprises a solution of the polysaccharide agent such as a modified pectin or amidated pectin. In some embodiments, the composition comprises a suspension of the polysaccharide agent. In some embodiments, the polysaccharide agent is dissolved or suspended in an aqueous solution.

To facilitate isolation of nucleic acids from the nucleic-acid containing samples, the polysaccharide agents described herein are added to the sample to achieve the final concentration of the polysaccharide agent of about 0.1 μg/mL to about 1000 μg/mL, from about 0.1 μg/mL to about 500 μg/mL, from about 0.1 μg/mL to about 200 μg/mL, from about 1 μg/mL to about 100 μg/mL, from about 1 μg/mL to about 50 μg/mL, or from about 1 μg to about 20 μg. In some embodiments, the polysaccharide agents are provided in the form of a stock solution or suspension, which, when added to the nucleic acid-containing sample, provides final concentration of the polysaccharide agent of about 0.1 μg/mL to about 1000 μg/mL, from about 0.1 μg/mL to about 500 μg/mL, from about 0.1 μg/mL to about 200 μg/mL, from about 1 μg/mL to about 100 μg/mL, from about 1 μg/mL to about 50 μg/mL, or from about 1 μg to about 20 μg. In other embodiments, the polysaccharide agents are dissolved or suspended in a lysis buffer which is then added to a nucleic acid-containing sample to facilitate lysing and isolation of the nucleic acid.

Other Components

In the methods disclosed herein, in addition to polysaccharide agents, the aqueous compositions can comprise any number of other agents, such as buffering agents, chelating agents, salts, defoaming agents, detergents, chaotropic agents, precipitating solvents, lysis agents, and/or organic additives. In the methods disclosed herein, any suitable combination of the other agents described herein can be used. For example, in some embodiments, the aqueous composition comprising a polysaccharide agent can comprise one or more buffering agents, chelating agents, salts, defoaming agents, detergents, chaotropic agents, precipitating solvents, lysis agents, organic additives, or combinations thereof.

A. Buffering Agents

In some embodiments, the compositions disclosed herein comprise one or more buffering agents that buffers the solution at a pH ranging from about pH 3.5 to about pH 9, from about pH 5 to about pH 8.5, from about pH 6 to about pH 8.5. In some embodiments, the buffering agent buffers the solution at a pH of about pH 6.6 to about 7.5, from about pH 6.7 to 7.4, from about pH 6.8 to about pH 7.3, or from about 6.9 to about 7.5. In some embodiments, the pH is buffered at about pH 7.05. In some embodiments, the concentration of the buffering agent ranges from about 10 mM up to about 100 mM, or from about 20 mM up to about 50 mM, or is about 50 mM. Any suitable buffering agent, such as buffering agents typically used in nucleic acid isolation can be included in the compositions disclosed herein, including but not limited to citrate buffer, Tris, phosphate, PBS, TAPS, Bicine, Tricine, TAPSO, HEPES, TES, MOPS, PIPES, Cacodylate, SSC, and IVIES.

In some embodiments, the compositions comprise HEPES or Tris. Typically, the buffering agent is present at about 100 mM, about 75 mM, about 50 mM, about 40 mM, or about 25 mM. The various buffering agents described above are intended to be illustrative; numerous other buffers suitable for use in nucleic acid isolation and analysis in accordance with the methods described herein are available to one skilled in the art.

B. Chelating Agents

In some embodiments, the compositions described herein comprise one or more chelating agents. Chelating agents are well known to those of skill in the art and include, but are not limited to N-acetyl-L-cysteine, ethylenediaminetetraacetic acid (EDTA), diethylene triamine pentaacetic acid (DTPA), ethylenediamine-N,N'-disuccinic acid (EDDS), 1,2-bis(o-aminophenoxy)ethane-N,N,N',N'-tetraacetic acid (BAPTA), and phosphonate chelating agents (e.g., including, but not limited to nitrilotris(methylene)phosphonic acid (NTMP), ethylenediamine tetra(methylene phosphonic acid) (EDTMP), diethylenetriamine penta(methylene phosphonic acid (DTPMP), 1-hydroxy ethylidene-1,1-diphosphonic acid (HEDP), and the like). In some embodiments, the chelating agent comprises EDTA or DTAP. In some embodiments, the chelating agent comprises EDTA. In some embodiments, when present, the chelating agent is present in the solution at a concentration ranging from about 5 mM to about 200 mM, or from about 10 mM to about 100 mM. In some embodiments, the chelating agent is present at a concentration of about 10 mM, about 20 mM, about 30 mM, about 40 mM about 60 mM, about 70 mM, about 80 mM, about 90 mM, or about 100 mM. In some embodiments, the chelating agent is present at a concentration of about 50 mM. In some embodiments, the concentration of the chelating agent ranges from about 1 mM up to about 140 mM, from about 5 mM up to about 100 mM, or from about 10 mM to about 50 mM.

C. Detergents or Surfactants

In some embodiments, the compositions described herein comprise one or more suitable detergents. In some embodiments, the detergent comprises an ionic detergent or a non-ionic detergent. Examples of suitable detergents include benzethonium chloride, CHAPS, CHAPSO, 1-Heptanesulfonic acid sodium salt, 1-Dodecanesulfonic acid sodium salt, n-lauroylsarcosine sodium salt, polysorbates such as Tween® 80 and Tween® 20, Brij 58, Sulfobetaine SB 12, Sulfobetaine SB 14, cetyltrimethylammonium bromide, cetylpyridinium chloride, PLURONIC® F-68, SDS, saponin, TRITON® X-100, and TRITON® X-114. Preferably, the detergent comprises polysorbate 20 such as Tween® 20. In some embodiments, the detergent is present in the solution at a concentration ranging from about 5 mM up to about 200 mM, from about 10 mM up to about 100 mM, from about 20 mM up to about 50 mM, or from about 30 mM up to about 40 mM. In some embodiments the detergent has a concentration of about 5 mM, about 10 mM, about 15 mM, about 20 mM, about 25 mM, about 40 mM, about 50 mM, about 75 mM, about 100 mM, about 150 mM, or about 200 mM. In some embodiments, the detergent is present at a concentration of about 35 mM. In some embodiments, the detergent is present at a percentage ranging from about 0.5% (v/v) up to about 30% (v/v), or from about 1% (v/v) up to about 20% (v/v) or from about 5% up to about 15% (v/v). In some embodiments, the detergent comprises about 0.1% to about 2% of said solution, or about 0.5% to about 1.5% of said solution, or about 1% of the polysaccharide agent solution by weight.

D. Lysis Agents

In some embodiments, the sample is lysed prior to the isolation of nucleic acids by contacting the sample with a lysis buffer. As used herein, "lysis buffer" means a buffer solution used for the purpose of breaking open cells. In some embodiments, lysis buffer comprises one or more polysaccharide agents disclosed herein. In some embodiments, the polysaccharide agents described herein are dissolved or suspended in the lysis solution. In some embodiments, the lysis solution comprises one or more lysis agents, for example, a protease. Suitable proteases include, but are not limited to serine proteases, threonine proteases, cysteine proteases, aspartate proteases, metalloproteases, glutamic acid proteases, metalloproteases, and combinations thereof. Illustrative suitable proteases include, but are not limited to proteinase k (a broad-spectrum serine protease), subtilisin trypsin, chymotrypsin, pepsin, papain, and the like. In some embodiments, the amount of protease is about 0.1 mg/mL, about 0.2 mg/mL, about 0.3 mg/mL, about 0.4 mg/mL, about 0.5 mg/mL, about 0.6 mg/mL, about 0.7 mg/mL, about 0.8 mg/mL, about 5 mg/mL, about 4 mg/mL, about 3 mg/mL, about 2 mg/mL, or about 1 mg/mL. Other suitable proteases are known to persons of skill in the art.

E. Chaotropic Agents

In some embodiments of the methods of the present invention, the compositions further comprise a suitable chaotropic agent. Examples of chaotropic agents include barium salts, alkali perchlorates, guanidinium hydrochloride, and guanidinium thiocyanate. Depending on its solubility, a chaotropic agent is typically used in the concentration ranges of between about 1 M and about 8 M. In some embodiments, guanidinium thiocyanate is used in the solutions and methods described herein.

F. Organic Additives

In some embodiments, the nucleic acid is isolated by precipitating onto, binding to, or immobilizing onto a solid substrate. In some embodiments, such precipitation, binding, and/or immobilization can be readily accomplished in the presence of an organic additive. In some embodiments, the organic additive is an organic solvent miscible with water. A variety of such solvents is known in the art. Exemplary solvents include alcohols, for example, lower alcohols (e.g., a $C_1$-$C_6$ alcohol). In some embodiments, the compositions can comprise ethanol or isopropanol. In some embodiments, the alcohol is ethanol. Alternatively, in some embodiments, polyethylene oxides or oligoethylene oxides can be used.

Other examples of organic additives suitable for use in the methods disclosed herein include, for example, agents selected from the group consisting of C3 and C4 alkyldioles, as well as short-chain ethylene glycol derivatives and diverse water-soluble polymeric compounds. These organic additives can be used substantially free of ethanol. Exemplary organic additives include 1,2-butanediol, 1,2-propanediol, 1,3-butanediol, 1-methoxy-2-propanolacetate, 3-methyl-1,3,5-pentanetriol, DBE-2 dibasic ester, DBE-3 dibasic ester, DBE-4 dibasic ester, DBE-5 dibasic ester, DBE-6 dimethyl adipate, diethylene glycol monoethyl ether (DGME), diethylene glycol monoethyl ether acetate (DGMEA), ethyl lactate, ethylene glycol, poly(2-ethyl-2-oxazoline), tetraethylene glycol (TEG), tetraglycol (tetrahydrofurfuryl polyethylene glycol ether), tetrahydrofurfuryl-polyethylene glycol 200, tri(ethylene glycol)-divinyl ether, dipropylene glycol monomethyl ether (DPGME), dipropylene glycol, triethylene glycol, and triethylene glycol monoethyl ether.

Nucleic Acid Isolation Methods

In some embodiments, the compositions described herein are used to isolate nucleic acids by precipitation onto a solid phase or support. In some embodiments, the solid phase or support comprises glass, silica, cellulose, or combinations thereof. The solid phase or support include the walls of a container, a fiber (e.g., glass fiber), a membrane (e.g., cellulose membrane), beads (e.g., magnetic beads, glass beads, cellulose beads, microparticles, or nanoparticles, etc.), and the like. In some embodiments, the solid phase is beads packed into a column. Any suitable solid support material can be used with the methods described herein, e.g., solid supports comprising a material selected from silica, glass, cellulose, ethylenic backbone polymer, polycarbonate, zeolite, and titanium dioxide.

In some embodiments, isolation or concentration of nucleic acid can be carried out by centrifugation or by filtration through porous materials, e.g. materials of defined pore size. In these instances, those skilled in the art will be able to optimize the recovery of nucleic acids by selecting a solid support of a suitable porosity.

In some embodiments, addition of the polysaccharide agents to samples of large volumes (e.g., about 5 mL or greater or about 10 mL or greater) facilitates isolation of nucleic acids from such samples, for example, by concentrating nucleic acids onto magnetic beads. This is particularly useful for pre-concentration of nucleic acids from diluted samples that are too large to be directly processed in microfluidic nucleic-acid detecting devices.

In some embodiments, addition of the polysaccharide agents allows all steps of the methods to be performed at room temperature. In some embodiments, the methods are suitable for isolation of nucleic acids at ambient temperature, e.g., temperatures between 15° C. and 35° C. In some embodiments, isolation of a nucleic acid using the methods disclosed herein can be performed in an automated cartridge, for example, the GeneXpert® (Cepheid, Sunnyvale, Calif., U.S.A) cartridge.

Nucleic Acids

As used herein, the term "nucleic acid" refers to any synthetic or naturally occurring nucleic acid, such as DNA or RNA, in any possible configuration, i.e., in the form of double-stranded nucleic acid, single-stranded nucleic acid, or any combination thereof. Nucleic acids include DNA, such as genomic DNA, and RNA, such as total RNA. Nucleic acids also include single-stranded or double-stranded nucleic acid, such as short double-stranded DNA fragments. In some embodiments, a synthetic nucleic acid can be isolated by the methods disclosed herein. In some embodiments, the nucleic acid is a circulating nucleic acid found in human plasma or blood.

In some embodiments, the methods described herein are used to precipitate nucleic acids from nucleic acid-containing solutions. Nucleic acid-containing solutions can be obtained by lysis of a nucleic-acid containing cell or material. Suitable nucleic acid-containing material includes blood, tissue biopsies, including sample such as paraffin-embedded tissue, smear preparations, spinal fluid, bacterial cultures, viral cultures, urine, semen, cell suspensions and adherent cells, PCR reaction mixtures, and in vitro nucleic acid modification reaction mixtures. The nucleic acid-containing material can comprise human, animal, bacterial, fungal, viral, or plant material. In other embodiments, the nucleic acid-containing solution can be obtained from a nucleic acid modification reaction or a nucleic acid synthesis reaction.

Nucleic Acid Detection Methods

The nucleic acids isolated using the methods and agents described herein are of suitable quality to be amplified to detect and/or to quantify one or more target nucleic acid sequences in the sample without requiring the removal of the polysaccharide agents. The nucleic precipitation methods and agents described herein are also applicable to basic research aimed at the discovery of gene expression profiles relevant to the diagnosis and prognosis of disease. The methods are also applicable to the diagnosis and/or prognosis of disease, the determination particular treatment regiments, and/or monitoring of treatment effectiveness.

The methods described herein simplify isolation of nucleic acids from biological samples and efficiently produce isolated nucleic acids well suited for use in PCR, RT-PCR, and sequencing systems. The methods of the present invention are compatible with known nucleic acid analysis and detection methods. In some embodiments, the nucleic acids isolated from a nucleic acid-containing sample using the methods described herein can be detected by any suitable known nucleic acid detection method. While in some embodiments the isolated nucleic acids are used in amplification reactions, other uses are also contemplated. Thus, for example, the isolated nucleic acids (or their amplification product(s)) can be used in various hybridization protocols including, but not limited to nucleic acid-based microarrays, and also in next generation sequencing (NGS) platforms.

Thus, in an aspect, disclosed herein is a method for detecting a nucleic acid in a sample, comprising: (a) contacting the sample with an aqueous composition comprising a polysaccharide agent disclosed herein; (b) concentrating the nucleic acid; and (c) detecting the nucleic acid. In some embodiments, the nucleic acid is concentrated by precipitation on a solid support.

In some embodiments, the detection method comprises nucleic acid amplification. Suitable non-limiting exemplary amplification methods include polymerase chain reaction (PCR), reverse-transcriptase PCR, real-time PCR, nested PCR, multiplex PCR, quantitative PCR (Q-PCR), nucleic acid sequence based amplification (NASBA), transcription-mediated amplification (TMA), ligase chain reaction (LCR), rolling circle amplification (RCA), and strand displacement amplification (SDA).

In some embodiments, the amplification method comprises an initial denaturation at about 90° C. to about 100° C. for about 1 to about 10 min, followed by cycling that comprises denaturation at about 90° C. to about 100° C. for about 1 to about 30 seconds, annealing at about 55° C. to about 75° C. for about 1 to about 30 seconds, and extension at about 55° C. to about 75° C. for about 5 to about 60 seconds. In some embodiments, for the first cycle following the initial denaturation, the cycle denaturation step is omitted. The particular time and temperature will depend on the particular nucleic acid sequence being amplified and can readily be determined by a person of ordinary skill in the art.

In some embodiments, the isolation and detection of a nucleic acid is performed in an automated sample handling and/or analysis platform. In some embodiments, commercially available automated analysis platforms are utilized. For example, in some embodiments, the GeneXpert system (Cepheid, Sunnyvale, Calif.) is utilized. However, the present invention is not limited to a particular detection method or analysis platform. One of skill in the art recognizes that any number of platforms and methods can be utilized.

The GeneXpert utilizes a self-contained, single use cartridge. Sample extraction, amplification, and detection of a nucleic acid can all be carried out within this self-contained "laboratory in a cartridge." See e.g., U.S. Pat. No. 6,374,684 which is herein incorporated by reference in its entirety. Components of the cartridge include, but are not limited to, processing chambers containing reagents, filters, and capture technologies useful to extract, purify, and amplify target nucleic acids. A valve enables fluid transfer from chamber to chamber and contains nucleic acids lysis and filtration components. An optical window enables real-time optical detection. A reaction tube enables very rapid thermal cycling. In some embodiments, the GenXpert system includes a plurality of modules for scalability. Each module includes a plurality of cartridges, along with sample handling and analysis components.

After the sample is added to the cartridge, the sample can be contacted with lysis buffer to release nucleic acids, and the released nucleic acids are isolated by contacting the lysed sample with an aqueous solution comprising a water-soluble polysaccharide comprising one or more uronic acid units and by subsequently precipitating the nucleic acid onto a solid substrate such as silica or glass substrate. In some embodiments, the water-soluble polysaccharide comprising one or more uronic acid units is dissolved in the lysis buffer. After precipitation, the supernatant is then removed, and the nucleic acids are eluted from the substrate with an elution buffer, for example, Tris/EDTA buffer. The eluate may then be processed in the cartridge to detect target genes of interest. In some embodiments, the eluate is used to reconstitute at least some of the PCR reagents, which are present in the cartridge as lyophilized particles. In some embodiments, the PCR uses Taq polymerase with hot start function, such as AptaTaq (Roche Inc., Basel, Switzerland).

In some embodiments, the methods described herein are used for isolating a nucleic acid (e.g., a DNA, an RNA) from a fixed paraffin-embedded biological tissue sample according any of the methods described herein, subjecting the precipitated nucleic acid to amplification using a pair of oligonucleotide primers capable of amplifying a region of a target nucleic acid, to obtain an amplified sample; and determining the presence and/or quantity of the target nucleic acid. In some embodiments, the target nucleic acid is a DNA (e.g., a gene). In some embodiments, the target nucleic acid is RNA (e.g., an mRNA, a non-coding RNA, and the like). In some embodiments, the nucleic acids isolated using the methods described herein are well suited for use in diagnostic methods, prognostic methods, methods of monitoring treatments (e.g., cancer treatment), and the like. Accordingly, in some illustrative, non-limiting embodiments, the nucleic acids extracted from fixed paraffin-embedded samples (e.g., from FFPET samples) can be used to identify the presence and/or the expression level of a gene, and/or the mutational status of a gene. Such methods are particularly well suited to identification of the presence, and/or expression level, and/or mutational status of one or more cancer markers. Accordingly, in some embodiments, the nucleic acids isolated using the methods described herein are utilized to detect the presence, and/or copy number, and/or expression level, and/or mutational status of one or more cancer markers.

Elution of Nucleic Acids

The detection and isolation methods disclosed herein can optionally include a washing step, i.e., the precipitated nucleic acid can be optionally washed on solid support for example, to remove components of the lysis buffer. Typically, a concentrated, e.g., precipitated nucleic acid is dissolved prior to detection. In some embodiments, the concentrated nucleic acid is dissolved in a buffer compatible with PCR reactions.

In some embodiments, for example, when a polyamine-modified polysaccharide is used to precipitate the nucleic acid, the precipitated nucleic acid can be eluted from the polyamine by contacting with a suitable eluting agent. In some embodiments, the eluting agent comprises ammonia or an alkali metal hydroxide. In some embodiments, the eluting agent has a basic pH. In some embodiments, the eluting agent has a pH of about 9 to about 12, about 9.5 to about 12, about 10 to about 12, or about 9 to about 11. Preferably, the pH of the eluting agent is above 10. Preferably, the eluting agent comprises ammonium hydroxide, NaOH, or KOH in a concentration sufficient for disrupting the binding of the nucleic acid with the polysaccharide agent. Exemplary eluting agents comprise 1% ammonia, 15 mM KOH, or 15 mM NaOH.

In some embodiments, the eluting agent comprises a polyanion. In some embodiments, the polyanion is a polymer comprising a plurality of anionic groups. In some embodiments, the anionic groups are phosphate, phosphonate, sulfate, or sulfonate groups, or combinations thereof. In some embodiments, the polyanion is a polymer negatively charged at pH above about 7. Both synthetic polyanions and naturally occurring polyanions can be used in the methods disclosed herein. In some embodiments, the polyanion is carrageenan. In some embodiments, the polyanion is a carrier nucleic acid. A carrier nucleic acid, as used herein, is a nucleic acid which does not interfere with the subsequent detection of the concentrated nucleic acid, for example, by PCR. Exemplary carrier nucleic acids include poly rA, poly dA, herring sperm DNA, salmon sperm DNA, and others. In some embodiments, the eluting agent comprises carrageenan and an alkali metal hydroxide, for example, NaOH or KOH. In some embodiments, the eluting agent comprises i-carrageenan and KOH.

While each of the elements of the present invention is described herein as containing multiple embodiments, it should be understood that, unless indicated otherwise, each of the embodiments of a given element of the present invention is capable of being used with each of the embodiments of the other elements of the present invention and each such use is intended to form a distinct embodiment of the present invention.

The referenced patents, patent applications, and scientific literature referred to herein are hereby incorporated by reference in their entirety as if each individual publication, patent or patent application were specifically and individually indicated to be incorporated by reference. Any conflict between any reference cited herein and the specific teachings of this specification shall be resolved in favor of the latter. Likewise, any conflict between an art-understood definition of a word or phrase and a definition of the word or phrase as specifically taught in this specification shall be resolved in favor of the latter.

As can be appreciated from the disclosure above, the present invention has a wide variety of applications. The invention is further illustrated by the following examples, which are only illustrative and are not intended to limit the definition and scope of the invention in any way.

EXAMPLES

All reagents were from commercial sources unless indicated otherwise.

Example 1: Preparation and Characterization of Polysaccharide Reagents

Synthesis of amine-modified acidic polysaccharides from commercially available materials has been accomplished according to one of the following procedures, as described below and summarized in Table 1, where EDA refers to ethylene diamine, DETA refers to diethylene triamine, DMPDA refers to 1,3-dimethyldipropylenediamine, AETMA refers to (2-Aminoethyl)trimethylammonium chloride hydrochloride, and TAEA refers to Tris(2-aminoethyl)amine.

General Procedure for Preparation of Amidated Polysaccharides (Methods A-G).

Starting polysaccharide (1 g) was added in portions to 50 mL of water (Methods B, D-G) or an amine solution (Methods A and C) and stirred for 30 min or until no visible solids were observed. When applicable, to this mixture, an appropriate coupling reagent was added (Methods D-F), and the mixture was stirred until it became homogenous. The resulting mixture was treated with an appropriate amount of amine (Methods B, D-G), and the mixture was further stirred magnetically at medium speed for the time specified in Table 1. Upon the completion of the reaction, the aqueous reaction mixtures (Methods A, B, and D-G) were diluted into 300 mL 1:1 acetone/methanol, and the slurry was stirred for 15 min before filtering. Filtered gel-like material was rinsed four times with methanol (50 mL). Methanolic reaction mixtures (Method C) were filtered directly without dilution into methanol. Precipitated modified polysaccharides were dried overnight in a vacuum oven at 45° C. When applicable, the dried pectin pellet was ground with mortar and pestle to yield a fine powder.

General Procedure for the Oxidation of Polysaccharides (Method H)

Polysaccharide (1 g) was suspended in water (50 mL) containing TEMPO (30 mg), and the suspension was cooled on ice. To the mixture was slowly added 18 mL of sodium hypochlorite solution (10-15% available chlorine), and the pH was monitored using a glass electrode and maintained near 10.8 by addition of 1M NaOH during the hypochlorite treatment. When the pH had stabilized, the reaction was quenched by the addition of 250 mL ethanol. The resulting precipitate was collected by filtration and rinsed with 60/30/10 isopropanol-water-concentrated HCl solution (3×50 mL) followed by methanol (3×50 mL). The remaining solid was dried in vacuo.

Extraction of Pectin from Aloe Vera Plant (Method I)

To 95 g of freshly collected Aloe Vera leaf slices, 65 mL ethanol was added, and the mixture was heated to 90° C. for 15 min. Then 200 mL of concentrated aqueous ammonia was added, and the mixture was heated to 90° C. with stirring for 30 min. The mixture was filtered through a glass filter, and the filtrate was passed through DEAE-cellulose column. The product was eluted with 1M $NaH_2PO_4$. The product eluate was dialyzed (~1 kDa membrane) thoroughly against molecular biology grade water, frozen, and lyophilized. The resulting solid was resuspended in aqueous ammonia.

General Procedure for the Modification of Pectin Via EDC/NHS Coupling with Pre-Hydrolysis Step (Methods K-L)

Starting polysaccharide (0.5 g) was added in portions to 50 mL of water and stirred for 60 min or until no visible solids were observed. 1M sodium hydroxide solution was added until pH was 12-13, and stirred for 20 min to hydrolyze any residual esters to carboxylates. The solution was carefully acidified with thorough stirring to pH 4.5-5.5 with 1M HCl. Then EDC.HCL (0.5 g) and NHS (0.15 g) as a solution in 5 mL of water were added, and the mixture was stirred for 1 hour at ambient temperature. Subsequently, the corresponding amount of amine was added as a solution in a minimal quantity of DI water, and the mixture was stirred for 22 hours at room temperature. Upon the completion of the reaction, the aqueous reaction mixtures were diluted into 300 mL of 1:1 acetone/methanol, and the slurry was stirred for 15 min before filtering. Filtered gel-like material was rinsed four times with methanol (50 mL). Precipitated modified polysaccharides were dried in a vacuum oven overnight at 45° C. The dried pellet was ground with mortar and pestle to yield a fine powder. To remove non-covalently bound amines from the product, the fine product powders were acid washed as described below.

To powdered pectin product was added 100 mL of acidic wash solution (isopropanol (550 mL), DI water (345 mL), concentrated hydrochloric acid (105 mL)), and the mixture was stirred magnetically for 30 min. The slurry was then filtered on a fritted glass filter, rinsed with acidic wash solution (3×25 mL) and then with neutral wash solution (isopropanol (590 mL) and DI water (345 mL); 3×25 mL). The resulting powder was dried in a vacuum oven at 50° C. overnight.

TABLE 1

Summary of synthetic methods used in the preparation of polysaccharide agents.

| Method | Solvent | Amine | Coupling Reagent | Reaction Time | T | Final ion exchange |
|---|---|---|---|---|---|---|
| A | N/A | Aq $NH_4OH$ (50 mL) | N/A | 72 hr | 25° C. | N/A |
| B | $H_2O$ (50 mL) | Alkylamine (10 mL) | N/A | 72 hr | 25° C. | N/A |
| C | N/A | 7N methanolic $NH_3$ (50 mL) | N/A | 72 hr | 25° C. | N/A |
| D | $H_2O$ (50 mL) | EDA (9 mL) | 420 mg EDC 438 mg HOBt•$H_2O$ | 24 hr | 25° C. | N/A |
| E | $H_2O$ (50 mL) | DETA (14.7 mL) | 420 mg EDC 438 mg HOBt•$H_2O$ | 24 hr | 25° C. | N/A |
| F | $H_2O$ (50 mL) | DMPDA (17.0 mL) | 420 mg EDC 438 mg HOBt•$H_2O$ | 24 hr | 25° C. | N/A |
| G | $H_2O$ (50 mL) | EDA (10 mL) | N/A | 72 hr | 25° C. | 10 mL 0.5M NaOH |
| J | $H_2O$ (50 mL) | TAEA (10 mL) | N/A | 24 hr | 25° C. | N/A |
| K | $H_2O$ (50 mL) | AETMA (0.5 g) | 500 mg EDC 150 mg NHS | 22 hr | 25° C. | Acid wash |
| L | $H_2O$ (50 mL) | Spermine (4 mL) | 500 mg EDC 150 mg NHS | 22 hr | 25° C. | Acid wash |

Synthesis of an Exemplary Polysaccharide Agent (Spermine-Modified Pectin) by NHS Coupling Apple pectin (10.0 g) was added to 1 L of Milli-Q filtered water and stirred for 1 h. 5 M NaOH (10 mL) was added, stirred for another 20 min, and then 1 N HCl (30 mL) was added (pH=4.2). N-(3-dimethylaminopropyl)-N'-ethylcarbodiimide hydrochloride (EDC, 10.08 g, 52.59 mmol) and N-hydroxysuccinimide (NHS, 3.026 g, 52.59 mmol) were added to the solution and stirred at RT for 1 h. Spermine (80 mL, 368 mmol) was added and the solution was stirred for 22 h at RT. The solution was then poured into rapidly stirring MeOH (2 L) and stirred for 20 min. The solids were collected by filtering the solution through a medium fitted glass funnel, and then washed with MeOH two times. The solids were dried under vacuum for 40 h at 50° C. The solids were ground to a fine powder using an electric coffee grinder and suspended in 500 mL of an acid wash solution (55% isopropyl alcohol, 34.5% water, and 10.5% concentrated hydrochloric acid) and stirred for 4.5 h. The solution was filtered off, and the solids were washed additionally twice with acid wash solution and then dried under vacuum overnight at 50° C. The solids were suspended in 750 mL of DI water and centrifuged at 4200 rpm using 50 mL centrifuge tubes for 10 min. Supernatants were collected and combined. The pellets were combined and suspended in 350 mL of DI water and centrifuged for 17 h at 4200 rpm using 50 mL centrifuge tubes. The supernatants were combined with the first supernatants. All of the combined supernatants were filtered through a 2-micron filter. The filtered solution was dried by lyophilization giving 7.78 g of spermine-pectin conjugate. Anal. Calc for $C_{16}H_{32}N_4O_5$ (galacturonic acid monomer plus spermine): C, 53.3; H, 8.95; N, 15.5. Found: N, 7.21.

Synthesis of an Exemplary Polysaccharide Agent (Spermine-Modified Pectin) by Oxidative Cleavage of Pectin Followed by Reductive Amination with Spermine In this example, a general procedure is provided for the modification of polysaccharide polymers with various polyamines through oxidation followed by reductive amination.

(A). Oxidation. Apple pectin (2.5 g) was added in portions to 250 mL deionized water with magnetic stirring until it has all dissolved. To this was added potassium periodate 2.43 g in portions with stirring and left stirring for 18 h. Reaction mixture was then dialyzed against water through 8 kd MWCO dialysis tubing over three. The resulting desalted polymer was subsequently lyophilized to give oxidized pectin as a crunchy off-white solid. The concentration of aldehydes can be readily measured via hydroxylamine titration (described in Zhao, H.; Heindel, N. D. J. Pharm. Res. 8(3), 400-402.) Aldehyde content determined to be 4.9 mmol/g (~1 eq aldehyde per polymer unit).

(B). Reductive amination. Oxidized pectin from step A (1.0 g) was suspended in 100 mL of deionized water, added spermine (1.32 g, 1.25 eq) and let stir for 18 h at room temperature. Added 1 g sodium borohydride pellet to the reaction and let stir for 18 h. The reaction mixture was then dialyzed against water through 8 kd MWCO dialysis tubing over three days and subsequently lyophilized to yield 200 mg of Compound 2 as off-white fluffy solid.

Characterization of Modified Polysaccharides

Size-exclusion chromatography, elemental analysis, and/or IR spectroscopy was used to characterize polysaccharides obtained by the methods A-L.

Elemental analysis was performed using a Perkin Elmer 2400 CHN analyzer. IR spectra were recorded by placing finely ground powders of the compounds on the IR detector crystal of a Perkin Elmer Frontier instrument equipped with a Universal ATR sampling accessory.

Table 2 summarizes the characterization of the modified polysaccharides. In Table 2, "A+" denotes the corresponding ammonium salt of the modifier amine, and "N/O" means the IR amide frequency was not observed; which is likely to due to overlap with other peaks.

TABLE 2

Chemical characterization of modified polysaccharides

| Compound | Starting material | Method | Modifier (A) | Counter ion* | weight % N | IR carboxylate peak frequency 1 (cm$^{-1}$) | IR carboxylate peak frequency 2 (cm$^{-1}$) | IR amide peak frequency (cm$^{-1}$) |
|---|---|---|---|---|---|---|---|---|
| 1 | PGA | A | NH$_4$OH | A$^+$ | 5.35 | 1579.9 | 1408.0 | N/O |
| 2 | PGA | B | NH$_2$(CH$_2$)$_2$NH$_2$ | A$^+$ | N/A | 1573.6 | 1403.3 | N/O |
| 3 | PGA | B | NH(CH$_2$CH$_2$NH$_2$)$_2$ | A$^+$ | 8.91 | 1578.3 | 1405.1 | N/O |
| 4 | PGA | B | (CH$_3$)$_2$N(CH$_2$)$_3$NH$_2$ | A$^+$ | 8.50 | 1582.1 | 1402.9 | N/O |
| 5 | PGA | C | NH$_3$ | A | 5.69 | 1579.9 | 1408.3 | N/O |
| 6 | PGA | D | NH$_2$(CH$_2$)$_2$NH$_2$ | A$^+$ | 5.70 | 1589.9 | 1412.1 | N/O |
| 7 | PGA | E | NH(CH$_2$CH$_2$NH$_2$)$_2$ | A | 8.23 | 1579.2 | 1405.0 | N/O |
| 8 | PGA | F | (CH$_3$)$_2$N(CH$_2$)$_3$NH$_2$ | A | 5.54 | 1585.0 | 1412.1 | N/O |
| 9 | PGA | G | NH$_2$(CH$_2$)$_2$NH$_2$/NaOH | Na$^+$ | 7.79 | 1591.91 | 1403.39 | N/O |
| 19 | Citrus pectin | A | NH$_4$OH | A$^+$ | 5.08 | 1591.6 | 1410.2 | 1673.3 |
| 20 | Citrus pectin | B | NH$_2$(CH$_2$)$_2$NH$_2$ | A$^+$ | 9.43 | 1585.1 | 1403.0 | N/O |
| 21 | Citrus pectin | B | NH(CH$_2$CH$_2$NH$_2$)$_2$ | A$^+$ | 13.23 | 1598.8 | 1402.9 | N/O |
| 22 | Citrus pectin | B | (CH$_3$)$_2$N(CH$_2$)$_3$NH$_2$ | A$^+$ | 5.59 | 1591.0 | 1403.5 | N/O |
| 23 | Citrus pectin | C | NH$_3$ | A$^+$ | 4.49 | 1591.5 | 1410.5 | 1670.3 |
| 24 | Citrus pectin | D | NH$_2$(CH$_2$)$_2$NH$_2$ | A$^+$ | 5.62 | 1591.0 | 1405.5 | N/O |
| 25 | Citrus pectin | E | NH(CH$_2$CH$_2$NH$_2$)$_2$ | A$^+$ | 9.31 | 1585.4 | 1392.7 | N/O |
| 26 | Citrus pectin | F | (CH$_3$)$_2$N(CH$_2$)$_3$NH$_2$ | A$^+$ | 4.82 | 1595.0 | 1406.9 | N/O |
| 27 | Citrus pectin | G | NH$_2$(CH$_2$)$_2$NH$_2$/NaOH | Na$^+$ | 7.85 | 1591.9 | 1401.4 | N/O |

TABLE 2-continued

Chemical characterization of modified polysaccharides

| Compound | Starting material | Method | Modifier (A) | Counter ion* | weight % N | IR carboxylate peak frequency 1 (cm$^{-1}$) | IR carboxylate peak frequency 2 (cm$^{-1}$) | IR amide peak frequency (cm$^{-1}$) |
|---|---|---|---|---|---|---|---|---|
| 28 | Apple pectin | A | NH$_4$OH | A$^+$ | 4.78 | 1593.9 | 1409.7 | 1667.7 |
| 29 | Apple pectin | B | NH$_2$(CH$_2$)$_2$NH$_2$ | A$^+$ | 6.56 | 1587.5 | 1409.87 | N/O |
| 30 | Apple pectin | B | NH(CH$_2$CH$_2$NH$_2$)$_2$ | A$^+$ | 11.06 | 1583.7 | 1406.9 | N/O |
| 31 | Apple pectin | B | (CH$_3$)$_2$N(CH$_2$)$_3$NH$_2$ | A$^+$ | 7.62 | 1578.6 | 1401.2 | N/O |
| 32 | Apple pectin | C | NH$_3$ | A$^+$ | 4.15 | 1593.6 | 1416.65 | 1667.7 |
| 33 | Apple pectin | D | NH$_2$(CH$_2$)$_2$NH$_2$ | A$^+$ | 8.56 | 1577.5 | 1406.0 | N/O |
| 34 | Apple pectin | E | NH(CH$_2$CH$_2$NH$_2$)$_2$ | A$^+$ | 11.05 | 1577.5 | 1406.9 | N/O |
| 35 | Apple pectin | F | (CH$_3$)$_2$N(CH$_2$)$_3$NH$_2$ | A$^+$ | 7.29 | 1591.4 | 1406.3 | N/O |
| 36 | Apple pectin | G | NH$_2$(CH$_2$)$_2$NH$_2$/NaOH | Na$^+$ | 5.43 | 1587.1 | 1407.2 | N/O |
| 57 | Pectin from citrus peel | N/A | N/A | N/A | N/A | N/A | N/A | N/A |
| 58 | Pectin from apple | N/A | N/A | N/A | N/A | N/A | N/A | N/A |
| 61 | Aloe extract EtOH + NH$_4$OH | I | NH$_4$OH | A$^+$ | | | | |
| 62 | Aloe extract NH$_4$OH | I | NH$_4$OH | A$^+$ | | | | |
| 72 | Apple pectin | B | ethanolamine | A$^+$ | | | | |
| 73 | Apple pectin | B | hydrazine | A$^+$ | | | | |
| 74 | Citrus pectin | B | ethanolamine | A$^+$ | | | | |
| 75 | Citrus pectin | B | hydrazine | A$^+$ | | | | |
| 76 | Citrus pectin | B | dimethylamino-propy lamine | A$^+$ | | | | |
| 77 | Citrus pectin | B | 4,7,10-trioxa-1,13-tridecanediamine | A$^+$ | | | | |
| 78 | Apple pectin | J | tris(2-aminoethyl)amine | A+ | 3.95 | | | |
| 79 | Apple pectin | K | (2-aminoethyl)-trimethylammonium chloride | H+ | 1.99 | | | |
| 80 | Apple pectin | L | spermine | H+ | 7.21 | | | |
| 81 | Apple pectin | L | tetraethylenediamine | H+ | 7.62 | | | |

Determination of molecular weights by High Performance Size Exclusion Chromatography High Performance Size Exclusion Chromatography with Evaporative Light Scattering detection (HPSEC-ELSD) was used to determine relative molecular weight (RMw) of polysaccharide agents. The chromatography was carried out on an Agilent HPLC system using Pullulan Series (Sigma Aldrich) as molecular weight calibration standards:
1.3 kDa: 53168 BCBS8194V;
12 kDa: 97873 8224V;
50 kDa: 43807 BCBT5326;
110 kDa: 47053 R4555V;
400 kDa: 18579 BCBT5321; and
800 kDa: 18789 BCBS8188.

Pullulan Series is a known in the art calibration standard for aqueous Size Exclusion Chromatography. Pullulan is a linear polysaccharide with units of maltotriose which are bonded via alpha-1,6 connection. Pullulan standards are typically used as molecular weight standards for Size Exclusion Chromatography of polysaccharides.

Agilent HPLC size exclusion column (Agilent PL aquagel MIXED—H column, 8 μm 300×7.5 mm) was used. Standard and sample solutions were prepared at 2 mg/mL in 0.05% NaN$_3$ solution by vortexing for 1 min and setting aside at room temperature until dissolved. The resulting solutions were filtered with a 0.45 um nylon syringe filter prior to the HPLC analysis. Using 10 mM ammonium bicarbonate (pH 7) mobile phase at 1 mL/min of flow rate, the standards and analyte samples were eluted within 30 min at the optimized ELSD conditions (70° C. of nebulizer, 80° C. of evaporator and 1.0 SLM of gas flow). Unlike typical integration of the standard peaks, the sample peaks are integrated with an integration event called "area sum slice" due to peaks' broadness.

Exemplary Results:

| Polysaccharide agent | Relative molecular weight |
|---|---|
| Compound 29 | 160-270 kDa |
| Compound 32 | 120-160 kDa |

Example 2: Recovery of RNA and DNA by Centrifugation

This experiment demonstrates that the polysaccharide agents can facilitate purification of DNA and RNA by precipitation using centrifugation. Compared to the commonly used ethanol precipitation procedure (Sambrook J, Russell D (2001) Molecular Cloning: A Laboratory Manual, 3rd edn. Cold Spring Harbor, N.Y.: Cold Spring Harbor Laboratory Press), the methods of the present invention significantly shorten the nucleic acid (NA) precipitation procedure and allow it to be carried out at room temperature, which advantageously makes the sample processing adaptable to automated NA analysis, such as cartridge-based NA analysis.

Nucleic acids (Genomic DNA, Promega, Madison, Wis. Cat #G3041, 202 ng/uL) and RNA Control (Life Technologies, Carlsbad, Calif. Cat #4307281, 50 ng/uL) were dissolved in 1×TE buffer at 5× desired final concentration (e.g. 5 μg/mL for final 1 μg/mL). Polysaccharide agents were dissolved in the appropriate buffer (CT/NG buffer prepared as described in U.S. Patent application 20160257998 and Viral and FFPE binding buffers prepared as described in U.S. Patent application 20170137871) at variable concentrations to provide 1, 5, and 20 μg of the agent in each test sample. The buffers without addition of polysaccharide agents were used as negative controls, and 0.3M sodium acetate with 70% EtOH (using the procedure of Sambrook and Russell (2001) Molecular Cloning: A Laboratory Manual (3rd ed.) Vol. 1-3, Cold Spring Harbor Laboratory, Cold Spring Harbor Press, N.Y.) was used as a 100% precipitating control.

To 100 uL of nucleic acid sample solution in a standard Eppendorf tube, 200 uL of a polysaccharide agent solution and 200 uL of EtOH were added. Samples were vortexed for 5 seconds to mix, then centrifuged at 12,000 g for 25 min to pellet the precipitated DNA. The supernatant was carefully decanted to avoid disrupting the pellet. The pellets were washed with chilled 70% EtOH solution and centrifuged for 10 min at 12,000 g, the supernatant was decanted, and the pellets were dried in a SpeedVac at a slightly elevated temperature (35° C.). 500 uL of TE buffer was added to each tube, and the pellet was re-suspended by vortexing at max speed for 30 seconds. Nucleic acids were quantified using Quantitative Fluorescent Picogreen DNA dye (Thermo) or Quantitative Fluorescent Ribogreen RNA dye (Thermo). Percent of recovery of nucleic acids was calculated by comparing the test samples to the 100% control. The results are summarized in Table 3.

TABLE 3

Recovery of nucleic acids by centrifugation in the presence of exemplary polysaccharide agents.

| | | Percent Recovery (Nucleic acid/Buffer) | | | | | | |
|---|---|---|---|---|---|---|---|---|
| Agent | Agent amount | E coli DNA/ CTNG | huRNA/ FFPE | huRNA/ pH 11 viral | huDNA/ CTNG | MS2 RNA/ pH 11 viral | MS2 RNA/ viral | MS2 RNA/ FFPE |
| NaOAc | 0.3M | 65.0 | 59.2 | 60.3 | 59.7 | 42.0 | 80.3 | 74.9 |
| None | N/A | 4.9 | 17.1 | 48.3 | 1.7 | 76.1 | 77.7 | 5.9 |
| Compound 1 | 1 μg | 18.6 | 93.1 | 71.2 | 12.8 | 43.2 | 73.3 | 6.9 |
| | 5 μg | 37.0 | 102.6 | 84.9 | 36.0 | 48.6 | 80.5 | 62.6 |
| | 20 μg | 53.1 | 73.1 | 77.2 | 89.1 | 68.6 | 80.7 | 55.4 |
| Compound 36 | 1 μg | 17.6 | 78.7 | 59.9 | 12.0 | 36.8 | 79.2 | 85.7 |
| | 5 μg | 23.9 | 94.1 | 77.4 | 86.1 | 52.7 | 79.4 | 97.6 |
| | 20 μg | 51.9 | 92.0 | 78.5 | 93.8 | 48.6 | 85.5 | 103.0 |
| Compound 32 | 1 μg | 17.2 | 74.2 | 77.4 | 40.7 | 45.9 | 82.3 | 6.1 |
| | 5 μg | 33.8 | 84.4 | 76.7 | 72.8 | 60.3 | 79.7 | 97.1 |
| | 20 μg | 63.0 | 85.2 | 76.4 | 91.5 | 72.1 | 81.7 | 95.1 |
| Compound 28 | 1 μg | 8.3 | 75.8 | 78.1 | 10.1 | 46.7 | 79.3 | 78.2 |
| | 5 μg | 22.1 | 85.8 | 75.7 | 13.5 | 59.8 | 82.3 | 91.7 |
| | 20 μg | 33.7 | 86.7 | 77.5 | 65.9 | 67.0 | 75.2 | 93.3 |
| Compound 21 | 1 μg | 17.2 | 94.6 | 67.1 | 15.9 | 55.9 | 76.6 | 83.3 |
| | 5 μg | 27.2 | 104.6 | 74.2 | 16.1 | 53.4 | 77.3 | 105.9 |
| | 20 μg | 36.3 | 98.4 | 73.6 | 21.2 | 65.2 | 70.6 | 106.4 |

Example 3: Recovery of RNA and DNA by Precipitation on a Filter Device

This experiment demonstrates that the polysaccharide agents can facilitate purification of DNA and RNA by precipitation on a filtration device, such as a membrane or a glass filter.

Nucleic acids (Genomic DNA, Promega, Madison, Wis., Cat #G3041, 202 ng/uL) and RNA Control (Life Technologies, Carlsbad, Calif. Cat #4307281, 50 ng/uL) were dissolved in 1×TE buffer at 5× desired final concentration (e.g. 5 μg/mL for final 1 μg/mL). Polysaccharide agents were dissolved in the appropriate buffer (CT/NG, Viral, and FFPE binding buffers as described in Example 2) at variable concentrations to provide 1, 5, and 20 μg of the agent in each test sample. The buffers without addition of agents were used as negative controls, and 0.3M sodium acetate with 70% EtOH (using the procedure of Sambrook et al.) was used as a 100% precipitating control.

To 100 uL of nucleic acid sample solution in a standard Eppendorf tube, 200 uL of a polysaccharide agent solution and 200 uL of EtOH were added. Samples were vortexed for 5 seconds to mix. The resulting lysates were passed through 0.8 um PES filter using a syringe filter device. The excess of the solution was removed by passing air through the filter. The precipitated material was eluted from the filter with 1 mL of the commercially available Tris elution buffer at 42° C. for 25 min. Nucleic acids were quantified using Quantitative Fluorescent Picogreen DNA dye or Quantitative Fluorescent Ribogreen RNA dye. Percent of recovery of nucleic acids was calculated by comparing the test samples to the 100% control. The results are summarized in Table 4.

TABLE 4

Recovery of nucleic acids by precipitation in the presence of exemplary polysaccharide agents

| Agent | Amount | Percent Recovery (Nucleic acid/Buffer) percent recovery | | | |
|---|---|---|---|---|---|
| | | huDNA/CTNG | huRNA/FFPE | MS2 RNA/viral | MS2 RNA/FFPE r |
| NaOAc | 0.3M | 5.5 | 2.8 | 1.8 | 18.2 |
| None | N/A | 0.0 | 0.0 | 2.6 | 1.7 |
| PGA | 1 ug | 67.8 | 62.3 | 57.3 | 60.8 |
| | 5 µg | 71.0 | 72.9 | 98.2 | 83.6 |
| | 20 µg | 96.6 | 52.1 | 70.7 | 57.8 |
| Compound 28 | 1 µg | 73.1 | 48.5 | 52.8 | 78.5 |
| | 5 µg | 94.2 | 66.2 | 89.8 | 74.9 |
| | 20 µg | 87.0 | 76.5 | 93.8 | 103.3 |
| Compound 32 | 1 µg | 83.9 | 29.4 | 78.6 | 37.5 |
| | 5 µg | 91.3 | 64.8 | 61.4 | 50.6 |
| | 20 µg | 40.2 | 68.2 | 94.1 | 86.4 |
| Compound 28 | 1 µg | 87.5 | 51.5 | 66.6 | 57.1 |
| | 5 µg | 102.5 | 63.2 | 86.4 | 90.0 |
| | 20 µg | 86.4 | 70.3 | 83.5 | 77.2 |
| Compound 21 | 1 µg | 71.1 | 62.8 | 61.8 | 78.3 |
| | 5 µg | 72.7 | 74.8 | 74.1 | 112.2 |
| Compound 21 | 20 µg | 4.4 | 81.0 | 72.4 | 91.7 |

Example 4: Isolation of Various Nucleic Acids

Example 4A. Isolation of Viral and Phage Nucleic Acids from Human Plasma

Preparation of Simulated Clinical Specimens

Plasma or Basematrix from pooled blood and inactivated viruses were used as simulated clinical specimens. Human plasma sample (1 mL) prepared from EDTA-preserved whole pooled blood (Bioreclamation, Westbury, N.Y.) or Basematrix (pooled from multiple individuals, Seracare Inc., Milford, Mass.) were treated with approximately 1 mg of Proteinase K (Roche Inc., Basel, Switzerland).

In the experiments demonstrating isolation of viral or phage nucleic acids, inactivated HIV, virus or MS2 Phage of known titer (all obtained from Zeptometrix Inc., Buffalo, N.Y.) were spiked directly into the plasma or Basematrix prior to isolation of nucleic acids. HIV was input at 10-1000 IU/mL concentrations into plasma or Basematrix. MS2 Phages were input up to 1e6 CFU/mL into plasma or Basematrix.

Nucleic acids were isolated from the simulated clinical samples in the presence of a polysaccharide agent according to the methods disclosed herein. Control samples were processed without the addition of a polysaccharide agent. Isolated nucleic acids were amplified by PCR or RT PCR. Delta Ct values are calculated as the difference between Ct values of the corresponding control (sample processed without the addition of a polysaccharide agent) and the samples processed with the addition of a polysaccharide agent.

Detection of Isolated Nucleic Acids by PCR and RT-PCR Assays

After isolation, viral nucleic acids were detected by a commercial method, e.g., using commercial kits (e.g., AmpliSens, Interlabservice, Russia). Any other detection method can be selected by one skilled in the art and used according to the manufacturer's instructions.

Tables 5 and 6 show results from testing of various polysaccharide agents for phage RNA extraction from plasma (Table 5); and viral RNA (HIV) extraction from plasma (Table 6). Nucleic acid recovered with or without the addition of polysaccharide agent was tested by the respective PCR and RT-PCR assays described above. Delta Ct values indicate the minimum difference between the Ct value obtained without the polysaccharide agent minus that obtained with addition of the polysaccharide agent.

TABLE 5

| Polysaccharide agent | ΔCt MS2 RNA |
|---|---|
| Compound 66 | 5.3 |
| Compound 67 | 10.2 |
| Compound 68 | 8.7 |
| Compound 69 | 12.8 |
| Compound 72 | 8.8 |
| Compound 73 | 9.8 |
| Compound 74 | 8.2 |
| Compound 76 | 10.7 |

TABLE 6

| Polysaccharide agent | ΔCt HIV |
|---|---|
| Compound 1 | 7 |
| Compound 2 | 7.5 |
| Compound 3 | 7.7 |
| Compound 4 | 7.3 |
| Compound 5 | 7.9 |
| Compound 6 | 8.2 |
| Compound 8 | 6.4 |
| Compound 19 | 5.4 |
| Compound 21 | 5.3 |
| Compound 23 | 3.0 |
| Compound 29 | 5.4 |
| Compound 32 | 3.4 |
| Compound 33 | 5.2 |
| Compound 39 | 4.5 |
| Compound 40 | 2.3 |
| Compound 41 | 2.8 |
| Compound 42 | 2.7 |
| Compound 78 | 10.1 |
| Compound 79 | 5 |
| Compound 80 | 5 |

Example 4B: Extraction of HBV Virus from Plasma or Basematrix

For HBV DNA extractions, ~100 copies of inactivated virus particles added per mL of human Basematrix were treated with 2 mg/mL proteinase K (Roche Inc., Basel, Switzerland) and incubated for 5 min at room temperature. Samples were then lysed with either one or two volumes of lysis buffer, vortexed, and split into aliquots containing differing concentrations of the exemplary polysaccharide agents. CT/NG lysis buffer was prepared as described in U.S. Patent application 20160257998 and Viral and FFPE lysis buffers were prepared as described in U.S. Patent application 20170137871. DNA was then precipitated by the addition of one or two volumes of binding reagents, vortexed, and transferred to V-E columns (Zymo Research, Irvine, Calif.) and spun according to the vendor's recommendations. The columns were then washed once with 70% ethanol and twice with HBV rinse reagent and spun according to the vendor's recommendations until the membrane became dry. The rinse reagent was comprised of KCl and also included polyethylene glycol of an approximate molecular weight of 200. Ideally, the polyethylene glycols used in the rinse can have a molecular weight range of from 200 to 8000 Da. Selection of a binding agent and/or rinse composition can optimized depending on sample type by those skilled in the art. Filters were then transferred to new centrifuge tubes and spun at maximum speed to completely dry the membrane. Each filter was then then transferred to a fresh collection tube. The filters were then incubated with an appropriate low salt elution buffer for one to five min at room temperature before being spun at the maximum speed in a table top centrifuge to collect the purified nucleic acid.

In the PCR assay, 200 nM concentrations of the following oligonucleotides were used in the reaction:

```
Forward primer:
                                (SEQ ID NO: 1)
GGCCATCAGCGCATGC Reverse primer:
                                (SEQ ID NO: 2)
CGGCTGCGAGCAAAACA Probe:
                                (SEQ ID NO: 3)
CCTCTGCCGATCCATACTGCGGAACTC
modified with FAM dye (5') and BHQ quencher (3')
```

Unless otherwise indicated in the text, PCR reaction mixtures were conducted in 20 uL volumes. Buffer compositions chosen based on vendor described conditions or adapted in a manner familiar to those skilled in the art. Real time PCR was performed on either a PCR Max Eco 48 (Cole Parmer, Vernon Hills, Ill.) or BioRad CFX Maestro (BioRad, Hercules, Calif.). The reaction mixtures were incubated at 95° C. for 60 sec., followed by 50 cycles of 10 Sec at 95° C. and 50 sec. at 60° C. The results are summarized in Table 7 below.

TABLE 7

Detection of isolated HBV by PCR reactions for HBV

| Compound | Amount Used | Binding Reagent | Lysis Buffer | Δ Ct |
|---|---|---|---|---|
| 33 | 25 to 75 μg | Ethanol | 4.5M GTC | 3.3 to 3.8 |
| 33 | 25 to 75 μg | DPGME | 4.5M GTC | 4.4 to 5.4 |
| 33 | 25 to 75 ug | Ethanol | 4.5M GTC | 4.9 to 5.2 |
| 33 | | Ethanol | 5M GuHCl | >10 |
| 33 | | PEG | 5M GuHCl | >10 |
| 33 | | Ethanol | 7M GuHCl | 6.7 |
| 33 | | DPGME | 7M GuHCl | 4.8 |
| 33 | | PEG | 7M GuHCl | 2.8 |
| 32 | | Ethanol | CT/NG | >10 |
| 32 | | Ethanol | viral | 7 |
| 32 | | PEG | viral | 3 |
| 32 | | Ethanol | 7M GuHCl | >10 |
| 32 | | PEG | 7M GuHCl | >10 |
| 30 | | Ethanol | CT/NG | 1.2 |
| 30 | | DPGME | CT/NG | 2.2 |
| 30 | | PEG | CT/NG | 1.3 |
| 30 | | Ethanol | viral | 6.5 |
| 30 | | DPGME | viral | 0.6 |
| 30 | | PEG | viral | 2.2 |
| 30 | | Ethanol | 5M GuHCl | 2 |

TABLE 7-continued

Detection of isolated HBV by PCR reactions for HBV

| Compound | Amount Used | Binding Reagent | Lysis Buffer | Δ Ct |
|---|---|---|---|---|
| 30 | | DPGME | 5M GuHCl | 1.3 |
| 30 | | PEG | 5M GuHCl | >10 |
| 30 | | Ethanol | 7M GuHCl | 0 |
| 30 | | DPGME | 7M GuHCl | 3.8 |
| 30 | | PEG | 7M GuHCl | 5.7 |
| 78 | | Ethanol | CT/NG | >10 |
| 78 | | Ethanol | viral | 2 |
| c78 | | PEG | 5M GuHCl | 1.5 |
| PGA | | Ethanol | viral | >10 |
| PGA | | DPGME | viral | 1.1 |
| PGA | | PEG | viral | 1.3 |
| PGA | | DPGME | 5M GuHCl | 0.7 |
| PGA | | PEG | 5M GuHCl | 2.8 |
| 3 | | PEG | CT/NG | >10 |
| 3 | | Ethanol | 7M GuHCl | 0.7 |
| 3 | | DPGME | 7M GuHCl | 0.4 |
| 6 | | Ethanol | CT/NG | >10 |
| 6 | | DPGME | CT/NG | 1.3 |
| 6 | | Ethanol | viral | 2.3 |
| 6 | | PEG | viral | 3.3 |
| 6 | | Ethanol | 7M GuHCl | 1.1 |
| 6 | | DPGME | 7M GuHCl | 1.2 |

Example 4C: Extraction of HIV Virus from Plasma or Basematrix

Inactivated HIV virus was extracted according to manufacturer's protocols using the Qiagen viral minElute (Qiagen, Hilden, Germany) column kit as per the manufacturer's instructions.

In the PCR assay, the following oligonucleotides (200 nM) were used:

```
Forward primer:
                                (SEQ ID NO: 4)
AATCCCCAAAGTCAAGGAGT Reverse primer:
                                (SEQ ID NO: 5)
ACTGTACCCCCCAATCC Probe:
                                (SEQ ID NO: 6)
CATCTTAAGACAGCAGTACAAATGGCAGT
modified with FAM dye (5') and BHQ quencher (3')
```

Unless otherwise indicated, PCR reaction mixtures were conducted in 20 uL volumes. Buffer compositions chosen based on vendor described conditions or adapted in a manner familiar to those skilled in the art. Real time PCR was performed on a PCR Max Eco 48. The reaction mixtures were incubated at 88° C. for 120 sec. and 300 sec. at 60° C., followed by 1 cycle at 90° C. for 20 sec., 70° C. for 30 sec. and 60 C for 10 sec. and then a stepdown cycling for 8 cycles with 10 sec. at 90° C., 69° C. stepping down 1° C. through 8 cycles to 62 vC for 30 sec., and 10 sec. at 60° C., followed by 40 cycles of 10 Sec at 90° C. and 40 sec. at 60° C. The results are summarized in Table 8 below.

TABLE 8

Detection of isolated HIV by PCR

| Compound | Binding Reagent | Lysis Buffer | Δ CT |
|---|---|---|---|
| 33 | Ethanol | minElute | 0.5 |
| 32 | Ethanol | minElute | 1.5 |

TABLE 8-continued

Detection of isolated HIV by PCR

| Compound | Binding Reagent | Lysis Buffer | Δ CT |
|---|---|---|---|
| 30 | Ethanol | minElute | 1.3 |
| 30 | Ethanol | 4.5M GTC | 0.7 |

Example 4D: Extraction of Nucleic Acids from Bacterial and Human Cells

Preserved *C. trachomatis* (CT), *N. gonorrhea* (NG), and human cells were prepared as a 10× solution in 10× Tris EDTA buffer (TE). Samples were then diluted in 1×TE buffer to make 1× samples such that the nucleic acids in the sample could be conveniently extracted and measured using a real time PCR assay. The cells were then lysed with one or two volumes of lysis buffer, vortexed, and incubated for 5 min at room temperature. CT/NG lysis buffer was prepared as described in U.S. Patent application 20160257998 and Viral and FFPE lysis buffers were prepared as described in U.S. Patent application 20170137871. The mixture was then split into samples containing differing concentrations of CP agents and incubated at 56 C with stirring for 5 min. DNA was precipitated with one or two volumes of an indicated binding reagent, vortexed, transferred to V-E columns (Zymo Research, Irvine, Calif.), and spun according to the vendor's recommendations. The columns were then washed once with 70% ethanol and twice with a rinse reagent and spun according to the vendor's recommendations until the membrane became dry. The rinse reagent was as described above. Filters were then transferred to new centrifuge tubes and spun at maximum speed to completely dry the membrane. Filters were then transferred to fresh collection tubes and then incubated with an appropriate low salt elution buffer for one to five min at room temperature before being spun at maximum speed in a table top centrifuge to collect the purified nucleic acid.

The following oligonucleotides were used (200 nM) were used in in the PCR assays detecting CT/NG/hgDNA:

```
CT forward primer
                                        (SEQ ID NO: 7)
GAAACACCGCCCG CT reverese primer:
                                        (SEQ ID NO: 8)
TTTGACCGGTTAAAAAAGAT CT probe:
                                        (SEQ ID NO: 9)
CCGCCCTTCAACATCAGTGAA
labeled with FAM dye (5') and BHQ quencher (3')

NG forward primer
                                        (SEQ ID NO: 10)
ACGCATGCTGATAGCGTCA NG reverese primer:
                                        (SEQ ID NO: 11)
TTGAGTTCTGCTTCCTCCTTG NG probe:
                                        (SEQ ID NO: 12)
CCGGAGATCCTTGCGATCCTTGCACC
labeled with FAM dye (5') and BHQ quencher (3')

hgDNA forward primer
                                        (SEQ ID NO: 13)
GCATTCCTGAAGCTGACAGCA hgDNA reverese primer:
                                        (SEQ ID NO: 14)
CTCCAGGCCAGAAAGAGAGAGTAG hgDNA probe:
                                        (SEQ ID NO: 15)
CCGTGGCCTTAGCTGTGCTCGC
labeled with FAM dye (5') and BHQ quencher (3')
```

Unless otherwise indicated in the text, PCR reaction mixtures were conducted in 20 uL volumes. Buffer compositions chosen based on the vendor described conditions or adapted in a manner familiar to those skilled in the art. Real time PCR was performed on either a PCR Max Eco 48 or BioRad CFX Maestro. The reaction mixtures were incubated at 95° C. for 120 sec, followed by 50 cycles of 10 sec at 95° C. and 50 sec at 60° C. The results are summarized in Tables 9-11 below.

TABLE 9

ΔCts for PCR reactions detecting CT

| Compound #: | Binding Reagent | Lysis Buffer | Δ CT |
|---|---|---|---|
| 33 | Ethanol | CT/NG | >10 |
| 33 | DPGME | CT/NG | 1.1 |
| 33 | PEG | CT/NG | 4.1 |
| 30 | DPGME | CT/NG | 2.5 |
| 30 | PEG | CT/NG | 2.4 |
| 32 | Ethanol | CT/NG | 2.6 |
| 32 | DPGME | CT/NG | 1.3 |

TABLE 10

ΔCTs for PCR reactions detecting NG

| Compound #: | Amount Used | Binding Reagent | Lysis Buffer | Δ CT |
|---|---|---|---|---|
| 33 | 37.5 to 150 µg | Ethanol | 7.4M GuHCl | 2.3 |
| 33 | 37.5 to 150 µg | Ethanol | 7.4M GuHCl | 2 |
| 33 | 37.5 to 150 µg | Ethanol | 7.4M GuHCl | 3.5 |
| 33 | 37.5 to 150 µg | Ethanol | CT/NG | 2.7 |
| 33 | 37.5 to 150 µg | Ethanol | CT/NG | 2.2 |
| 33 | 37.5 to 150 µg | Ethanol | CT/NG | 3 |
| 33 | | DPGME | CT/NG | 1.3 |
| 33 | | PEG | CT/NG | 4.5 |
| 33 | | Ethanol | 5M GuHCl | 2.4 |
| 33 | | DPGME | 5M GuHCl | 2.3 |
| 33 | | PEG | 5M GuHCl | >10 |
| 30 | | Ethanol | CT/NG | 2.8 |
| 30 | | DPGME | CT/NG | 2.4 |
| 30 | | PEG | CT/NG | 5.7 |
| 30 | | Ethanol | 5M GuHCl | 2.6 |
| 30 | | DPGME | 5M GuHCl | 5.8 |
| 78 | | DPGME | CT/NG | 4.1 |
| 30 | | PEG | 5M GuHCl | >10 |
| PGA | | DPGME | CT/NG | 2.6 |
| 32 | | Ethanol | 5M GuHCl | 2 |
| 32 | | DPGME | 5M GuHCl | 1 |
| 32 | | PEG | 5M GuHCl | >10 |

TABLE 11

Detection of isolated hgDNA by PCR

| Compound #: | Binding Reagent | Lysis Buffer | Δ CT |
|---|---|---|---|
| 33 | DPGME | CT/NG | 1.2 |
| 33 | Ethanol | 5M GuHCl | >10 |
| 32 | DPGME | CT/NG | 2.1 |
| 32 | Ethanol | 5M GuHCl | >10 |
| 30 | DPGME | CT/NG | 2.6 |
| 30 | PEG | CT/NG | >10 |
| 6 | Ethanol | CT/NG | 1.5 |
| 6 | DPGME | CT/NG | 1.2 |
| 3 | DPGME | CT/NG | 4.3 |
| PGA | DPGME | CT/NG | 3.5 |

Example 4E: Extraction of Fragmented MTB DNA from 2 mL of Plasma Using a Column (Zymo Research)

Fragmented MTB DNA (fMTB DNA 200-400 bp) was added to 2 mL of plasma samples (BioIVT) treated with 0.1 mL of 2 mg/mL proteinase K (Roche Inc., Basel, Switzerland) and incubated for 5 min at room temperature. Samples were then lysed with 3 mL of viral lysis buffer, vortexed, and 0.005 mL of a 2.5% solution of compound 33 was added. CT/NG, Viral and FFPE lysis buffers were prepared as described above. DNA was then precipitated by the addition of 3 mL of ethanol, vortexed, and transferred to Zymo Research V-E columns and spun according to the vendor's recommendations. The columns were then washed once with one milliliter of 70% ethanol and twice with one milliliter of a rinse reagent and spun according to the vendor's recommendations until the membrane became dry. The rinse reagent was comprised of KCl and also included polyethylene glycol of an approximate molecular weight of 200. Filters were then transferred to new centrifuge tubes, spun at maximum speed to completely dry the membrane, then transferred to fresh collection tubes, incubated with 0.1 mL of an appropriate low salt elution buffer for 1-5 min at room temperature before being spun at maximum speed in a table top centrifuge to collect the purified nucleic acid. PCR was performed as described for the Xpert MTB/RIF Ultra Assay by Chakravorty et al. mBio, 2017 Volume 8 Issue 4 e00812-17.

TABLE 12

PCR detection of isolated fragmented MTB DNA

| Compound | μL (1% solution) | ΔCt |
|---|---|---|
| 30 | 3 | 5.7 |
| 30 | 6 | No result |
| 78 | 3 | 5.4 |
| 78 | 6 | 5.7 |
| PGA | 3 | 3.3 |
| PGA | 6 | 4 |
| 6 | 3 | 4.8 |
| 6 | 6 | 4.2 |
| 3 | 3 | No result |
| 3 | 6 | 5 |

Example 4F: Extraction of Fragmented MTB DNA from Plasma or Urine Samples Using a Zymo Research Column Fragmented MTB DNA (fMTB DNA 200-400 bp) was added to plasma or urine samples (BioIVT) treated with 0.25 mL of 2 mg/mL proteinase K (Roche) and incubated for 5 min at room temperature. Samples were then lysed with 7.5 mL of viral lysis buffer, vortexed, and 0.005 mL of a 2.5% solution of compound 33 was added. CT/NG, Viral, and FFPE lysis buffers were prepared as described above. DNA was then precipitated by the addition of 7.5 mL of ethanol, vortexed, and transferred to Zymo Research V-E columns and spun according to the vendor's recommendations. The columns were then washed once with one milliliter of 70% ethanol and twice with one milliliter of HBV rinse reagent and spun according to the vendor's recommendations until the membrane became dry. The rinse reagent was comprised of KCl and also included polyethylene glycol of an approximate molecular weight of 200. Filters were then transferred to new centrifuge tubes and spun at maximum speed to completely dry the membrane. Filters were then transferred to fresh collection tubes, incubated with 0.1 mL of an appropriate low salt elution buffer for 1-5 min at room temperature before being spun at maximum speed in a table top centrifuge to collect the purified nucleic acid. Controls for this experiment were prepared by spiking the same amount of fMTB DNA directly into a separate RT-PCR reaction in order to have a comparison indicative of 100% extraction and recovery efficiency. PCR was performed as described for the Xpert MTB/RIF Ultra Assay by Chakravorty et al. mBio, 2017 Volume 8 Issue 4 e00812-17. The results are shown in Tables 13 and 14 below.

TABLE 13

Detection of MTB DNA extracted from urine (4-5 mL) using Compound 33 with different amounts of lysis buffer, saturated salt solution, and binding reagent (ethanol, isopropyl alcohol, dipropylene glycol methyl ether, polyethylene glycol MW 8000). ΔCts are calculated as the difference between the sample Ct and a 100% spike in control.

| Urine (mL) | Viral Lysis Buffer (mL) | $NH_4Cl$ saturated (mL) | Compound 33 (2.5%) (μl) | Binding Reagent (mL) | ΔCt |
|---|---|---|---|---|---|
| 5 | 7.5 | 3 | 5 | EtOH (10) | 0.7 |
| 5 | 7.5 | 3 | 5 | EtOH (12.5) | 2.2 |
| 5 | 7.5 | 3 | 5 | EtOH (15) | 20.1 |
| 5 | 7.5 | 3 | 5 | IPA (3) | 3.3 |
| 5 | 7.5 | 3 | 5 | IPA (5) | 2.3 |
| 5 | 7.5 | 3 | 5 | IPA (7) | 1.9 |
| 5 | 7.5 | 3 | 5 | EtOH (10) | −0.3 |
| 5 | 7.5 | 3 | 10 | EtOH (10) | 0 |
| 5 | 7.5 | 3 | 15 | EtOH (10) | 0.2 |
| 5 | 7.5 | 3 | 20 | EtOH (10) | 0 |
| 4 | 5 | 2 | 5 | EtOH (5) | 6.8 |
| 4 | 5 | 2 | 5 | EtOH (5.5) | 5.7 |
| 4 | 5 | 2 | 5 | EtOH (6) | 2.2 |
| 4 | 5 | 2 | 5 | EtOH (6.5) | 1.1 |
| 4 | 5 | 2 | 5 | EtOH (7) | 1.4 |
| 4 | 5 | 2 | 5 | EtOH (7.5) | 3.4 |
| 4 | 5 | 2 | 5 | EtOH (8) | 3.6 |
| 4 | 4 | 1.92 | 5 | IPA (4.8) | 0.9 |
| 4 | 4 | 1.92 | 5 | EtOH (6.4) | 2.5 |
| 4 | 4.5 | 1.92 | 5 | 4.8 IPA | 1.2 |
| 4 | 4 | 1.92 | 5 | IPA (5.5) | 1.05 |
| 4 | 4.5 | 1.92 | 5 | IPA (5.5) | 0.8 |
| 4 | 5 | 2 | 5 | 6 IPA | 0.9 |
| 4 | 5 | 2 | 5 | DPGME (6) | 1.3 |
| 4 | 5 | 2 | 5 | DPGME (5.5) | 1.8 |
| 4 | 4.5 | 2 | 5 | IPA (5.5.) | 0.9 |
| 4 | 4.5 | 1.75 | 5 | IPA (5.5.) | 0.8 |
| 4 | 4.5 | 2.25 | 5 | IPA (5.5.) | 1.3 |
| 4 | 5 | 2 | 5 | IPA (5.5.) | −0.2 |
| 4 | 4 | 1 | 5 | 40% PEG8k (6) | 2.1 |
| 4 | 4 | 1 | 5 | 40% PEG8k (8) | 2.8 |
| 4 | 4 | 2 | 5 | 40% PEG8k (6) | 1.6 |
| 4 | 5 | 1 | 5 | 40% PEG8k (6) | 1.5 |
| 4 | 4 | 2 | 5 | 40% PEG8k (4) | 3.9 |

TABLE 13-continued

Detection of MTB DNA extracted from urine (4-5 mL) using Compound 33 with different amounts of lysis buffer, saturated salt solution, and binding reagent (ethanol, isopropyl alcohol, dipropylene glycol methyl ether, polyethylene glycol MW 8000). ΔCts are calculated as the difference between the sample Ct and a 100% spike in control.

| Urine (mL) | Viral Lysis Buffer (mL) | NH₄Cl saturated (mL) | Compound 33 (2.5%) (μl) | Binding Reagent (mL) | ΔCt |
|---|---|---|---|---|---|
| 4 | 4 | 2 | 5 | 40% PEG8k (3) | 3.5 |
| 4 | 5 | 2 | 5 | 40% PEG8k (4) | 3.3 |
| 4 | 5 | 2 | 5 | 40% PEG8k (3) | 5 |

TABLE 14

Detection of MTB DNA extracted from plasma (5 mL) using Compound 33 lysis buffer, saturated salt solution, and binding reagent (ethanol). ΔCt is calculated as the difference between the sample Ct and a 100% spike in control.

| Plasma (mL) | Viral Lysis Buffer (mL) | NH₄Cl saturated (mL) | Compound 33 (2.5%) (μl) | Binding reagent (mL) | ΔCt from 100% control |
|---|---|---|---|---|---|
| 5 | 7.5 | 3 | 5 | EtOH (7.5) | 0 |

Example 4G: Extraction of Fragmented MTB DNA from Urine or Plasma Samples Using a Centrifuge Five milliliters of plasma to which fragmented MTB DNA (fMTB DNA 200-400 bp) were added were mixed with 0.25 mL of Proteinase K solution (~2 mg/mL) and allowed to incubate briefly. Then five milliliters of viral lysis buffer were added along with five milliliters of saturated ammonium sulfate. The mixture was then centrifuged for 10 min at high speed in a table top centrifuge. The supernatant was collected and to it was added 0.01 mL of a 10% (w/v) glycogen solution, 0.005 mL of Compound 33 solution (CP15 1%), 7.5 mL of viral lysis buffer and 15 mL of ethanol. The mixture was then spun for 20 min in a table top centrifuge at high speed. The supernatant was discarded and the pellet was rinsed with 70% ethanol and spun down for 5 min in a table top centrifuge at high speed. After the wash was discarded the pellet was dried briefly and 0.1 mL of low salt elution buffer was added. After incubation the elution buffer was collected and analyzed further by RT-PCR. Longer elution times up to 60 min were found to improve yields. Controls for this experiment were prepared by spiking the same amount of fMTB DNA directly into a separate RT-PCR reaction in order to have a comparison indicative of 100% extraction and recovery efficiency. PCR was performed as described for the Xpert MTB/RIF Ultra Assay by Chakravorty et al. mBio, July/August 2017 Volume 8 Issue 4 e00812-17

Results are shown in Table 15 below.

TABLE 15

Shows ΔCts from extractions of MTB DNA from urine and plasma. Cts are compared to a 100% control.

| Sample (5 mL) | ΔCt from 100% control |
|---|---|
| Urine | 0.1 |
| Plasma | 0.1 |

Example 5: Effect of Polysaccharide Agent Concentration on DNA Recovery by Precipitation This experiment demonstrates that the polysaccharide agents facilitate the isolation of nucleic acids in a concentration-dependent manner.

The precipitation of human genomic DNA by filtration was carried out as described above. Nucleic acids (Genomic DNA, Promega, Madison, Wis. Cat #G3041, 202 ng/uL) and RNA Control (Life Technologies, Carlsbad, Calif. Cat #4307281, 50 ng/uL) were dissolved in 1×TE buffer at 5× desired final concentration (e.g. 5 μg/mL for final 1 μg/mL). Polysaccharide agents were dissolved in the appropriate buffer (for example, CT/NG buffer as described above) at variable concentrations of the agent in each test sample. The results are summarized in Table 16.

TABLE 16

Percentage of human genomic DNA captured on 0.8 um PES filter as a function of polysaccharide agent concentration. Percentage was determined by preparing a theoretical 100% control, dividing the fluorescence value of the sample tested by the value of the theoretical control minus blank.

| Concentration (μg/mL) | Polysaccharide Percent recovery hgDNA | | | | | | | | | |
|---|---|---|---|---|---|---|---|---|---|---|
| | .01 | .05 | .1 | .2 | | 5 | 0 | 00 | 50 | 00 |
| PGA | .1 | .5 | .8 | .0 | .7 | 7.6 | 6.2 | 0.3 | 0.3 | 2.1 | 4.1 |
| 32 | .1 | .0 | .0 | .3 | .1 | 2.8 | 2.6 | 6.4 | 1.7 | 0.9 | 2.5 |
| 36 | .0 | .0 | .8 | .1 | .0 | 4.5 | 8.4 | 7.5 | 8.0 | 9.2 | 8.3 |
| 21 | .1 | .0 | .5 | .4 | .9 | 5.5 | 2.7 | 4.5 | 7.2 | 9.9 | 3.1 |

Example 6: Magnetic Bead-Based Extraction of HBV Viral DNA from Plasma

This example demonstrates that polysaccharide agents facilitate precipitation of viral DNA on magnetic beads. The precipitated DNA eluted from the beads is of suitable quality to be detected by amplification methods such as PCR without any additional steps to remove the agent.

Human plasma sample (0.25 mL) prepared from EDTA-preserved whole blood (Bioreclamation, Westbury, N.Y.)

was spiked with HBV virus and extracted using the Dynabead SILANE viral NA Kit (Invitrogen, Carlsbad, Calif.) according to the manufacturer's protocol. DNA extracted from clinical specimens was amplified via RT-PCR technology commercially available in the AmpliSenS HBV FRT Monitor Kit as per the manufacturer's instructions. Polysaccharide agents were used at a concentration of 20 µg per prep. The following were combined to prepare each sample: 1440 uL Human Plasma, 160 mL HBV (50 kU/mL), and 400 uL Proteinase K 6 (Roche Inc., Basel, Switzerland). The following agents were used: (a) 2× no polysaccharide agent (control) in Lysis Buffer; (b) 2× Compound 21 in Lysis Buffer; and (c) 2× Compound 32 in Lysis Buffer.

To 250 uL of sample in a 2 mL centrifuge tube, 300 uL Lysis/Binding Buffer (viral NA) were added. Depending on the tested condition, 1.4 uL of each sample with lysis buffer was replaced with 1.4 uL of either Compound 21 or Compound 32 solution. The mixtures were incubated at room temperature for 5 min, and 150 uL isopropanol was added to each tube. To each tube, 50 uL of freshly resuspended Dynabeads (Invitrogen, Carlsbad, Calif.) were added, and the contents were mixed and incubated at room temperature for 10 min (while mixing at low speeds). The tubes were placed the on magnetic stand for 2 min, and supernatant was removed with a pipette. The beads were resuspended in 850 uL of the kit's Washing Buffer 1, precipitated by placing the tube on the magnetic stand for 1 min. The washing procedure was repeated, and then the beads were resuspended in 450 uL of the kit's Washing Buffer 2. The samples were transferred to new centrifuge tubes in order to reduce contamination, and the second washing step was repeated. The beads were dried for 10-15 min, and 100 uL the kit's Elution Buffer (viral NA) was added to each tube. After incubation for 3 min at 70° C., the beads were resuspended and then precipitated by placing the samples back on the magnetic stand for 2 min. The supernatant containing extracted nucleic acids was transferred into fresh test tubes for use in downstream PCR or for storage at −80° C.

TABLE 17

RT-PCR detection of viral nucleic acids (Ct) precipitated from samples on the magnetic beads using commercial RT-PCR reagents (AmpliSenS HBV FRT Monitor Kit, InterLab Service Ltd., Russia).

| Additive | Compound 29 | Compound 32 | None |
|---|---|---|---|
| HBV Ct | 31.8 | 31.7 | 34.2 |

This experiment demonstrates that nucleic acids isolated using the methods of the invention are amplifiable by PCR without any additional steps for removal of the polysaccharide agents from the isolated nucleic acid.

Example 7: Extraction of Nucleic Acids from Larger Volumes of Water, Urine, and Plasma with Magnetic Beads and Polysaccharide Agents This experiment demonstrates that the methods of nucleic acid isolation disclosed herein are suitable for isolation of nucleic acids from larger volume (greater than 5 mL) samples.

A. Recovery of Nucleic Acids from Plasma.

A 10 mL of human plasma sample prepared from EDTA-preserved whole blood (Bioreclamation, Westbury, N.Y.) was treated with approximately 10 mg of Proteinase K (Roche Inc.) and mixed with an equal volume lysis reagent (containing 3-5M guanidinium thiocyanate, 0.1%-1% w/v Tween® 20.) preferably to a final concentration of about 1.8M and adjusted to a pH preferably between 7 and 8. To this mixture, 70-100% polyethylene oxide 200 or an equal volume of ethanol was then added to a final concentration of about 30-40%. The sample was mixed for 10 min on a shaker. Magnetic beads (Agencourt AMPure XP beads, Beckman Coulter, Brea, Calif., used as specified in the kit instructions) and polysaccharide agents (Compound 29, 50 µg/mL of plasma) were added to the mixture, while for control experiments, only magnetic beads were added. The samples were put onto a magnetic stand for 10 min. If no magnetic beads were used, the samples were centrifuged for 10 min at 4000 g.

1. Wash and Elution Procedures:

The centrifuged pelleted material or magnetic beads (1 mL), derived from the entire mixture ranging in volume from 30-40 mL, and the nucleic acids released in the lysate are then bound to a track etched filter with defined pore sizes, preferably between 0.4-1 um. The fiber or filter is subsequently washed with a mixture of 1-2 M guanidinium thiocyanate and 60-100% polyethylene oxide 200 or an alternative additive such as ethanol. Subsequently the fiber or filter is rinsed with polyethylene oxide 200-containing buffer, and then the total DNA is eluted into ca. 80 uL Tris/EDTA buffer (20 mM Tris).

2. PCR and RT-PCR Assays of Viral and Human Nucleic Acid Extracted from Clinical Specimens The extracted human genomic DNA was amplified by PCR as described above. Alternatively, PCR primers and probes to the following human genes were used for detection of extracted DNA: GUS B, SDH A, TUB B, RPL P0. The enzyme utilized for PCR was AptaTaq DNA polymerase (Roche Inc., Basel, Switzerland) at 10 U per reaction. PCR was carried out for 45 cycles of 10 second denaturation steps at 95° C. and 40 second anneal/extension cycles at 64° C. The results demonstrating superior recovery of DNA with the addition of an exemplary polysaccharide agent to the magnetic beads are demonstrated in Table 11, showing that a significant reduction in the Ct values was achieved when a polysaccharide agent was added to the sample.

B. Recovery of Nucleic Acids from Urine.

A 10 mL sample of human urine, obtained via informed consent from healthy volunteers, was mixed with an equal volume of guanidinium thiocyanate lysis reagent (containing 3-5M guanidinium thiocyanate, 0.1%-1% w/v Tween® 20). preferably to a final concentration of about 1.8M and adjusted to a suitable pH, preferably between 7 and 8. Samples were processed and detection of the nucleic acid by PCR was performed as described above for the recovery of nucleic acids from large volumes of plasma. A representative result is demonstrated in Table 11, showing that a significant reduction in the Ct values was achieved when an exemplary polysaccharide agent was added to the sample.

This result demonstrates that addition of an exemplary polysaccharide agent facilitates recovery of nucleic acids from large volumes of urine.

C. Recovery of Nucleic Acids from Water.

A 10 mL water sample was spiked with 290 ng of human genomic DNA sourced from Promega Corporation (Madison, Wis.) and mixed with an equal volume guanidinium thiocyanate lysis reagent (containing 3-5 M guanidinium thiocyanate, 0.1%-1% w/v Tween® 20). preferably to a final concentration of about 1.8M and adjusted to a pH preferably between 7 and 8. To this mixture, 70-100% polyethylene oxide 200 or an equal volume of ethanol was then added to a final concentration of the organic reagent of about 30-40. Samples were processed and detection of the nucleic acid by PCR was performed as described above. A representative result is shown in Table 18, showing that a significant reduction in the Ct values was achieved when an exemplary polysaccharide agent was added to the sample. This result demonstrates that addition of a polysaccharide agent facilitates recovery of nucleic acids from large volumes of water.

TABLE 18

The human genomic DNA extracted from 10 mL sample volumes of water, urine, or human plasma with Beckman Coulter magnetic beads (Beckman Coulter, Brea, CA) in the presence or absence of Compound 29 was amplified by PCR with primers and probes to the GUS B human gene. The enzyme utilized for PCR was AptaTaq DNA polymerase (Roche Inc., Basel, Switzerland) at 10 U per reaction. Average Ct and Standard Deviations are shown for experiments replicated either 7 or 8 times.

| Sample | Additive | Average Ct | Std. Dev. |
|---|---|---|---|
| 10 mL water | Compound 29 | 33.2 | 0.6 |
| 10 mL water | None | 36.5 | 0.8 |
| 10 mL plasma | Compound 29 | 30.5 | 0.6 |
| 10 mL plasma | None | 37.6 | 1 |
| 10 mL urine | Compound 29 | 29.4 | 1.1 |
| 10 mL urine | None | 33 | 0.8 |

In separate experiments, the same procedure was followed using larger volumes of urine (5-10 mL), except that no magnetic beads were used and only the polysaccharide agent was added to the mixture. Extending the findings from the studies using magnetic beads, the inventors discovered that the polysaccharide agents themselves facilitate collection and concentration of cell-free nucleic acids from the larger volume samples, for instance, by flocculation, and the flocculated nucleic acids could be further concentrated by centrifugation. Following extraction of the nucleic acid aggregates it was discovered that the concentrations of DNA recovered are equivalent to those that could be collected with magnetic beads using a protocol prescribed by the kit manufacturer.

Example 8: Recovery of hgDNA by Centrifugation with the Aid of a Polyamine-Amidated Pectin This example demonstrates that polyamine-polysaccharide agents can be used to isolate nucleic acids from solutions by centrifugation. The extracted nucleic acid is then released and detected via PCR. The extracted DNA is of suitable quality to be detected by amplification methods such as PCR, without any additional steps to remove the agent.

Compound 80 (spermine-modified pectin) was dissolved in water and pH was adjusted with 1M NaOH to produce a 1% solution at pH 10.5.

Nucleic acid (Genomic DNA, Promega, Madison, Wis.) Cat #G3041, 202 ng/uL) was dissolved in deionized water (1 μg/500 μl). To 500 ul of nucleic acid sample solution in a standard Eppendorf tube (2 mL), a corresponding amount of 1% polymer solution was added to give a 10 ug polymer spiked hgDNA-polymer solution. Equal amounts of ethanol (500 μl) and guanidine thiocyanate (4.5 M, 500 μl) were then added to the sample. As a control, samples were also prepared without the addition of any polysaccharide agent solution.

Samples were vortexed for 5 seconds to mix, then centrifuged at 20,000 rpm for 25 min at 5° C. to pellet the precipitated DNA. The supernatant was carefully decanted to avoid disrupting the pellet. The pellets were washed with chilled 70% EtOH solution and centrifuged for 10 min at 20,000 rpm, the supernatant was decanted, and the pellets were dried in a SpeedVac at a 40° C. Nucleic acids were eluted by adding 20 ul of 15 mM KOH containing 0.04% w/v i-carrageenan, placing the samples on thermomixer at 1250 rpm at 42° C. for 5 min, and then centrifuging briefly.

hgDNA was quantified by PCR as described above using standard buffers and Phoenix enzyme from Qiagen Inc. Extra Tris buffer (20 mM pH 8.6) was added to the PCR master mix to assist in neutralizing the elution buffer. PCR was carried out after an initial 30 s denaturation at 95° C. for 45 cycles (5 s denaturation at 93° C. and 30 s anneal/extension at 69° C.).

PCR results are summarized in Table 12 demonstrating recovery of nucleic acids from water using an exemplary method of nucleic acid isolation. Ct values from PCR amplification of hgDNA obtained from 1:1:1 water/ethanol/guanidine thiocyanate 4.5M centrifugation spiked with 1 μg hgDNA, with and without addition of spermine-modified pectin agent are shown. DNA spike control (100% control) was a sample that contained no hgDNA treated in the same manner as the hgDNA-containing samples, with 1 μg hgDNA spiked in before PCR. The results are summarized in Table 19.

TABLE 19

Ct values from amplification of recovered hgDNA

| Additive | Average Ct | Std. deviation |
|---|---|---|
| None | >45 | n/a |
| Compound 80, 10 μg | 43.3 | 1.5 |
| Compound 80, 40 μg | 37.7 | 0.7 |
| 100% control (no additive) | 30.8 | |

Example 9: Recovery of hgDNA by Centrifugation with a Polyamine-Amidated Pectin from Water This example demonstrates that polyamine-modified polysaccharide agents can be used to extract nucleic acid from a simple aqueous solution without the need for other additives such as other solvents or salts. The extracted nucleic acid is then released and detected via PCR. The extracted DNA is of suitable quality to be detected by amplification methods such as PCR, without any additional steps to remove the agent.

Compound 80 (spermine-modified pectin) was dissolved in water to produce a 1% solution.

Nucleic acid (Genomic DNA, Promega, Madison, Wis.) Cat #G3041, 202 ng/uL) was dissolved in deionized water (1 mL). To 1 mL of nucleic acid sample solution in a standard 1.5 mL centrifuge tube a corresponding amount of 1% polymer solution was added to give 10, 50, 100 and 200 μg polymer spiked hgDNA-polymer solution. No other solvents or solutions were added to the sample. As a control a sample was also prepared without the addition of any polymer solution.

Samples were vortexed for 5 seconds to mix, then centrifuged at 20,000 rpm for 25 min at 25° C. to pellet the precipitated DNA. The supernatant was carefully decanted to avoid disrupting the pellet. The pellets were washed with chilled 70% EtOH solution (2 mL) and centrifuged for 25 min at 25,000 rpm, the supernatant was decanted, and the pellets were dried in a SpeedVac at 40° C. Nucleic acid was eluted by adding 25 ul of 15 mM KOH containing 0.04% w/v i-carrageenan, placing the sample on thermomixer at 1250 rpm at 42° C. for 5 min, and then centrifuging briefly.

hgDNA was quantified by PCR as described above by comparison to the 100% control, and the results are shown in Table 20. The polyamine-amidated polysaccharide significantly increased the yield of recovered DNA from the aqueous sample compared to the no polymer control. Compound 29 was also included to demonstrate the significantly higher extraction efficiency of a polyamine modified pectin (Compound 80) versus a diamine-modified pectin (Compound 29). DNA spike control (100% control) was a sample that contained no hgDNA treated in the same manner as the hgDNA-containing samples, with 1 µg hgDNA spiked in before PCR. The results are summarized in Table 20.

TABLE 20

Ct values from amplification of recovered hgDNA

| Additive | Average Ct | Std. deviation |
|---|---|---|
| None | 33.9 | 0.3 |
| Compound 80, 10 µg | 30.1 | 0.6 |
| Compound 80, 50 µg | 28.9 | 0.2 |
| Compound 80, 100 µg | 28.5 | 0.1 |
| Compound 80, 200 µg | 28.9 | 0.3 |
| 100% spiked control | 29.8 | 0.3 |
| Compound 29, 10 µg | 33.9 | 0.4 |
| Compound 29, 50 µg | 33.5 | 0.2 |
| Compound 29, 100 µg | 33.4 | 0.1 |
| Compound 29, 200 µg | 33.1 | 0.1 |

To demonstrate the importance of having a negatively charged polymer (i.e. polyanion such as carrageenan) in the elution buffer when using exemplary polysaccharide reagents amidated with a diamine, e.g., polyamine-modified pectins, PCR samples were prepared as described above, with and without carrageenan. 10, 50, 100, and 200 µg of Compound 80 (used as 1% solution in water) was added to 20 µL aliquots of 15 mM KOH with 0.04% carrageenan and 1 µg hgDNA. To this mock elution buffer was added 80 ul of PCR master mix (preparation described in example 7 and 8). Table 21 demonstrates the effect of carrageenan on PCR of hg DNA recovered from pellets treated with spermine-modified pectin (Compound 80). No amplification is reported as Ct=45. No amplification is detected without the addition of carrageenan in the elution buffer.

TABLE 21

Ct values from amplification of hgDNA isolated with the aid of compound 80 without the addition of carrageenan in the elution agent

| Additive | Average Ct | Std. deviation |
|---|---|---|
| Compound 80, 10 µg | >45 | n/a |
| Compound 80, 50 µg | >45 | n/a |
| Compound 80, 100 µg | >45 | n/a |
| Compound 80, 200 µg | >45 | n/a |
| 100% control | 30.8 | 0.3 |

While illustrative embodiments have been illustrated and described, it will be appreciated that various changes can be made therein without departing from the spirit and scope of the invention.

What is claimed is:

1. A method for isolation of a nucleic acid from a sample comprising a nucleic acid, comprising:
   (a) contacting a sample comprising a nucleic acid with an aqueous composition comprising a polysaccharide comprising one or more repeating units having the structure of Formula II:

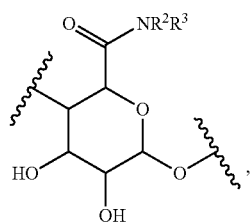

(II)

or a stereoisomer, a salt, a tautomer, or a combination thereof, wherein:
   $R^2$ and $R^3$ are independently H, substituted $C_1$-$C_8$ alkyl, substituted $C_3$-$C_8$ cycloalkyl, substituted $C_3$-$C_8$ heterocycloalkyl, or substituted $C_2$-$C_{20}$ heteroalkyl; and
   (b) concentrating the nucleic acid on a solid support thereby isolating the nucleic acid, wherein the method is performed in a cartridge.

2. The method of claim 1, wherein the polysaccharide further comprises one or more repeating units of Formula (III):

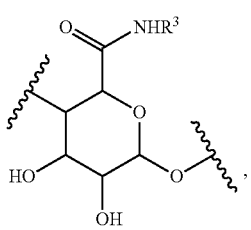

(III)

or a stereoisomer, a salt, a tautomer, or a combination thereof, wherein $R^3$ is H, $CH_3$, $CH_2CH_2NH_2$, $CH_2CH_2N(CH_3)_2$, $CH_2CH_2OH$, $(CH_2)_2O(CH_2)_2NH_2$, or $CH_2CH_2NHCH_2CH_2NH_2$.

3. The method of claim 1, wherein the polysaccharide comprises one or more repeating units having the structure of Formula VI:

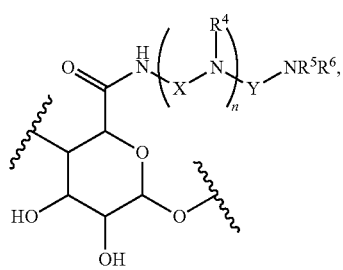

(IV)

or a stereoisomer, a salt, a tautomer, or a combination thereof, wherein:

n is 0, 1, 2, or 3;
$R^4$ is H or $C_1$-$C_3$ alkyl;
X, at each occurrence, is independently $C_2$-$C_4$ alkylene or $C_4$-$C_6$ heteroalkylene;
Y is a $C_2$-$C_3$ alkylene or $C_4$-$C_6$ heteroalkylene; and
$R^5$ and $R^6$ are independently H or $C_1$-$C_3$ alkyl.

4. The method of claim 1, wherein the polysaccharide comprises one or more repeating units having the structure of Formula V:

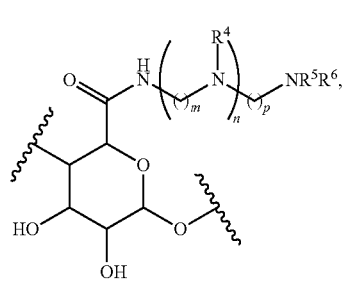

(V)

or a stereoisomer, a salt, a tautomer, or a combination thereof, wherein:
   n is 0, 1, 2, or 3;
   m, at each occurrence, is independently 2, 3, or 4;
   p is 2, 3, or 4;
   $R^4$ is H or $C_1$-$C_3$ alkyl; and
   $R^5$ and $R^6$ are independently H or $C_1$-$C_3$ alkyl.

5. The method of claim 1, wherein the polysaccharide comprises one or more repeating units represented by Formula VI, Formula VII, or Formula VIII:

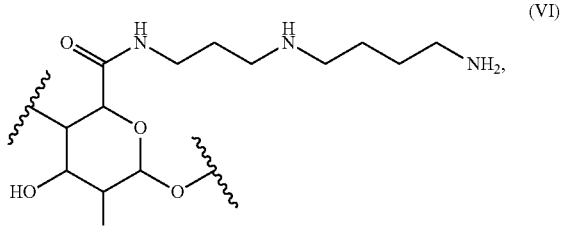

(VI)

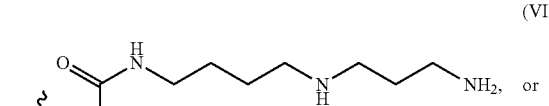

(VII)

(VIII)

or a stereoisomer, a salt, a tautomer, or combination thereof.

6. The method of claim 1, wherein the polysaccharide is present in the aqueous composition at a concentration from about 0.1 μg/mL to about 1000 μg/mL.

7. The method of claim 1, wherein the polysaccharide has a relative molecular weight between about 120 kDa and about 500 kDa.

8. The method of claim 1, wherein the nucleic acid is concentrated by centrifugation, precipitation, or a combination thereof.

9. The method of claim 1, wherein the nucleic acid is concentrated by precipitation on a solid support.

10. The method of claim 1, wherein the solid support comprises a material selected from silica, glass, ethylenic backbone polymer, mica, polycarbonate, zeolite, titanium dioxide, or a combination thereof.

11. The method of claim 1, wherein the solid support is a magnetic bead, glass bead, cellulose filter, polycarbonate filter, polytetrafluoroethylene filter, polyvinylpyrrolidone filter, polyethersulfone filter, or glass filter.

12. The method of claim 1, wherein the method further comprises washing and/or eluting the nucleic acid concentrated on the solid support with a wash agent, an eluting agent, or a comniation thereof.

13. The method of claim 1, wherein the aqueous composition further comprises one or more of a lysis agent, a chaotropic agent, a salt, a buffering agent, a surfactant, or a defoaming agent.

14. The method of claim 1, wherein the sample comprising nucleic acid is or comprises blood, plasma, serum, semen, spinal fluid, tissue biopsy, tear, urine, stool, saliva, smear preparation, bacterial culture, mammalian cell culture, viral culture, human cell, bacteria, extracellular fluid, PCR reaction mixture, cell lysate preparation, or in vitro nucleic acid modification reaction mixture.

15. A method for isolation of a nucleic acid from a sample comprising a nucleic acid, comprising:
(a) contacting a sample comprising a nucleic acid with an aqueous composition comprising a polysaccharide comprising one or more repeating units having the structure of Formula II:

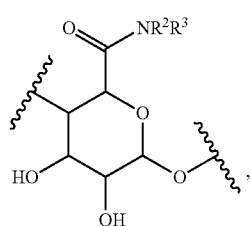

(II)

or a stereoisomer, a salt, a tautomer, or a combination thereof, wherein:
$R^2$ and $R^3$ are independently H, substituted $C_1$-$C_8$ alkyl, substituted $C_3$-$C_8$ cycloalkyl, substituted $C_3$-$C_8$ heterocycloalkyl, or substituted $C_2$-$C_{20}$ heteroalkyl; and
(b) concentrating the nucleic acid on a solid support thereby isolating the nucleic acid, further comprising contacting the sample with a lysis buffer prior to contacting the sample with the aqueous composition.

16. The method of claim 15, wherein the polysaccharide comprises one or more repeating units having the structure of Formula IV:

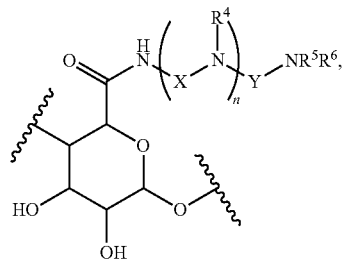

(IV)

or a stereoisomer, a salt, a tautomer, or a combination thereof, wherein:
n is 0, 1, 2, or 3;
$R^4$ is H or $C_1$-$C_3$ alkyl;
X, at each occurrence, is independently $C_2$-$C_4$ alkylene or $C_4$-$C_6$ heteroalkylene;
Y is a $C_2$-$C_3$ alkylene or $C_4$-$C_6$ heteroalkylene; and
$R^5$ and $R^6$ are independently H or $C_1$-$C_3$ alkyl.

17. The method of claim 15, wherein the polysaccharide comprises one or more repeating units represented by Formula VI, Formula VII, or Formula VIII:

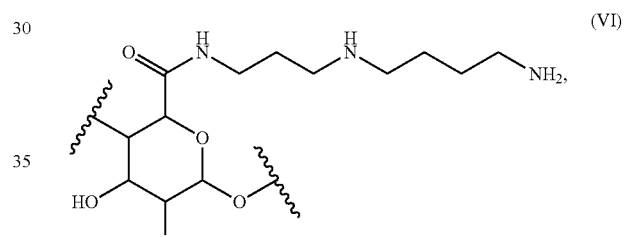

(VI)

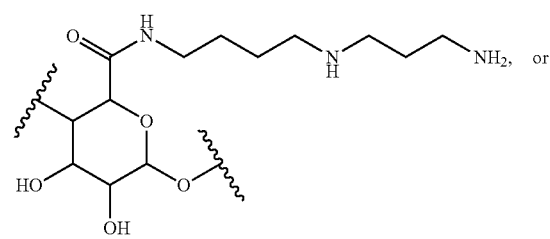

(VII)

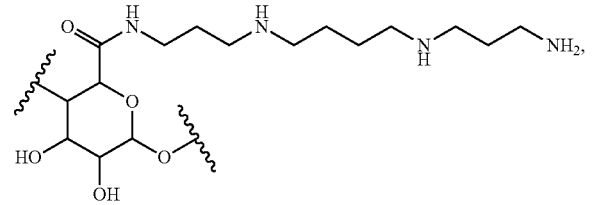

(VIII)

or a stereoisomer, a salt, a tautomer, or combination thereof.

18. A method for detecting a nucleic acid in a sample, comprising:
(a) contacting the sample with an aqueous composition comprising a polysaccharide comprising one or more repeating units having the structure of Formula II:

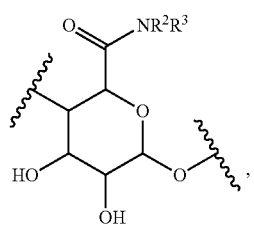

(II)

or a stereoisomer, a salt, a tautomer, or a combination thereof, wherein:

$R^2$ and $R^3$ are independently H, substituted $C_1$-$C_8$ alkyl, substituted $C_3$-$C_8$ cycloalkyl, substituted $C_3$-$C_8$ heterocycloalkyl, or substituted $C_2$-$C_{20}$ heteroalkyl;

(b) concentrating the nucleic acid; and (c) detecting the nucleic acid, wherein detecting the nucleic acid comprises amplifying the nucleic acid by polymerase chain reaction.

19. The method of claim 18, wherein the polysaccharide comprises one or more repeating units having the structure of Formula IV:

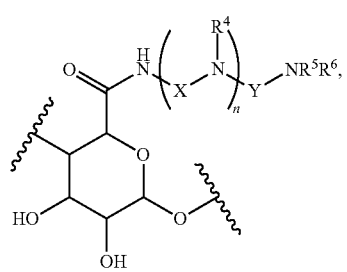

(IV)

or a stereoisomer, a salt, a tautomer, or a combination thereof, wherein:

n is 0, 1, 2, or 3;

$R^4$ is H or $C_1$-$C_3$ alkyl;

X, at each occurrence, is independently $C_2$-$C_4$ alkylene or $C_4$-$C_6$ heteroalkylene;

Y is a $C_2$-$C_3$ alkylene or $C_4$-$C_6$ heteroalkylene; and $R^5$ and $R^6$ are independently H or $C_1$-$C_3$ alkyl.

* * * * *